(12) United States Patent
Li et al.

(10) Patent No.: US 11,840,554 B2
(45) Date of Patent: Dec. 12, 2023

(54) CATION EXCHANGE RESINS

(71) Applicant: BRISTOL-MYERS SQUIBB COMPANY, Princeton, NJ (US)

(72) Inventors: Zhengjian Li, Sudbury, MA (US); Xuankuo Xu, Boxborough, MA (US); Chao Huang, Shrewsbury, MA (US); Zhiqiang Chen, Hudson, MA (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 299 days.

(21) Appl. No.: 17/172,156

(22) Filed: Feb. 10, 2021

(65) Prior Publication Data

US 2021/0246161 A1 Aug. 12, 2021

Related U.S. Application Data

(63) Continuation of application No. 16/324,595, filed as application No. PCT/US2017/046223 on Aug. 10, 2017, now Pat. No. 10,947,268.

(60) Provisional application No. 62/374,337, filed on Aug. 12, 2016.

(51) Int. Cl.
| | |
|---|---|
| C07K 1/18 | (2006.01) |
| C07K 16/00 | (2006.01) |
| B01J 39/07 | (2017.01) |
| B01J 39/20 | (2006.01) |
| B01J 39/22 | (2006.01) |
| C07K 1/22 | (2006.01) |

(52) U.S. Cl.
CPC ............ *C07K 1/18* (2013.01); *B01J 39/07* (2017.01); *B01J 39/20* (2013.01); *B01J 39/22* (2013.01); *C07K 1/22* (2013.01); *C07K 16/00* (2013.01); *C07K 2317/14* (2013.01); *C07K 2319/30* (2013.01)

(58) Field of Classification Search
CPC .......... C07K 1/18; C07K 1/22; B01D 15/361; B01D 15/362; B01J 39/00; B01J 39/16; B01J 39/18
See application file for complete search history.

(56) References Cited

U.S. PATENT DOCUMENTS

2010/0267932 A1  10/2010  Eon-Duval et al.

FOREIGN PATENT DOCUMENTS

| WO | 2007108955 A1 | 9/2007 |
| WO | 2012078376 A1 | 6/2012 |
| WO | 2013006670 A2 | 1/2013 |
| WO | 2013066707 A1 | 5/2013 |

OTHER PUBLICATIONS

Chen et al. "Insights in understanding aggregate formation and dissociation in cation exchange chromatography for a structurally unstable Fc-fusion protein" Journal of Chromatography A, 1460, p. 110-122, 2016; available online Jul. 9, 2016 (Year: 2016).*
Tsutomu Arakawa, et al., "Suppression of protein interactions by arginine: A proposed mechanism of the arginine effects", Biophysical Chemistry 127 (2007) 1-8.
Zhiqiang Chen, et al., "Insights in understanding aggregate formation and dissociation in cation exchange chromatography for a structurally unstable Fc-fusion protein", Journal of Chromatograpy A, 1460 (2016) 110-122.

* cited by examiner

*Primary Examiner* — Ryan B Huang

(57) ABSTRACT

In some embodiments, the present invention provides a method of purifying a protein of interest with a reduced level of aggregation formation in cation exchange (CEX) chromatography, comprising: (a) providing a mixture comprising the protein of interest and one or more contaminants; (b) loading the mixture onto a CEX resin coupled with arginine; and (c) eluting the protein of interest from the resin, thereby purifying the protein of interest with a reduced level of aggregation formation in CEX chromatography.

4 Claims, 16 Drawing Sheets

1    2    3    4    5    6

CATION EXCHANGE RESINS

CROSS REFERENCE TO RELATED INVENTION

This application is a continuation of U.S. application Ser. No. 16/324,595 filed Feb. 11, 2019 now allowed, which is a 35 U.S.C. § 371 National Stage patent application of International Application PCT/US2017/046223, filed Aug. 10, 2017, which claims priority to U.S. Provisional Application No. 62/374,337, filed Aug. 12, 2016, the contents of which are specifically incorporated by reference herein.

BACKGROUND OF THE INVENTION

Monoclonal antibodies (mAbs) and their derivative products (e.g., Fc-fusion proteins) play an important role in treating some of the most challenging human diseases owing to the safety, efficacy and high quality of these types of biologics [1]. The monoclonal antibody market is growing significantly fast, and it is estimated that the combined world-wide sales of monoclonal antibody products will reach approximately $125 billion by 2020 [2]. Therefore, the development of robust commercial chromatography purification processes is of vital importance to patients [3]. Purification processes typically use Protein A chromatography for capture, followed by one or two polishing steps [4]. For those mAbs and Fc-fusion proteins possessing basic isoelectric points (pI), cation-exchange chromatography (CEX) has traditionally been considered a preferred option for polishing step, mainly due to relatively simple column behaviors, efficient removal of product-related impurities (e.g., HMW), and generally minor impact of electrostatic interactions on protein structure [5, 6]. In comparison, proteins often undergo partial unfolding upon adsorption on surfaces of hydrophobic interaction chromatography (HIC) media [7-9].

In recent years, there has been an increasing number of cases reporting rather unconventional protein binding and elution behaviors in CEX. For example, Voitl et al. [10, 11] reported a two-peak elution profile during a linear salt gradient for human serum albumin on Fractogel EMD SE Hicap. Since no HMW increase was observed in the two elution peaks, it was hypothesized that the protein bound to the resin in two different conformations requiring different salt concentrations to fully elute. Gillespie et al. [12] reported a two-peak elution profile for an unstable aglycosylated IgG1 in several CEX resins using a linear salt gradient, and that the late eluting peak contained more aggregates than the early eluting peak. Hydrogen-deuterium exchange and Fourier transform infrared spectroscopy (FTIR) results indicated that the second peak was originated by resin-induced antibody denaturation which could be mitigated by using preferentially excluded solutes, such as arginine [13-15]. The work evaluated many factors related to CEX operation, however, the aggregation mechanisms were not discussed in detail. Guo and Carta [16-18] reported a two-peak CEX elution behavior for a glycosylated IgG2. This effect was prominent for a polymer-functionalized resin Fractogel EMD $SO_3^-$, but virtually absent for a macroporous resin without grafted polymer (e.g. UNOsphere Rapid S), leading to the hypothesis that protein diffusion through the tentacle polymer destabilized protein structure and caused aggregate formation. It was noted that the two-peak elution behavior was seen only when the bound protein was held for extended period of time. Luo et al. [19] reported a two-peak elution behavior of an IgG2 upon salt elution. The work suggested that the IgG2 can form reversible self-association (RSA) at high salt and high protein concentration, and that the RSA species can bind more strongly to the resin than monomer, contributing to the peak splitting. In another study, Luo et al. [20] reported a split peak phenomenon for an IgG4, and linked it to the separation of histidine-protonation-based charge variants.

Diversified column behaviors for biologic therapeutics can ultimately be attributed to their complex molecular properties. For example, although mAbs and Fc-fusion proteins share similar fragment crystallizable (Fc) regions, their solution properties can differ significantly due to the highly variable complementarity determining region (CDR) and the glycosylation in the Fc region [21]. It has been reported that some mAbs are prone to denaturation and aggregation at low pH (pH 2-4) and high salt concentration [22]. Buchner et al. [23] reported that immunoglobulin can form an "A-state" under low pH (<3), which is characterized by a high degree of secondary structure with increased hydrophobicity and a tendency towards slow aggregation in high salt. Latypov et al. [24, 25] conducted an extensive study for human IgG1 and IgG2 on acid-induced unfolding and aggregation which was primarily determined by the stability of the $CH_2$ domain located in the Fc region. Depending on solution conditions, proteins such as mAbs can partially unfold and form irreversible aggregates or reversible clusters with each other while maintaining their native structure [26, 27]. Reversible or irreversible mAb association is often driven by protein-protein attractions due primarily to heterogeneous charge distribution on the mAb surface especially at high protein concentration [28-30], whereas recent report on the formation of dimeric IgG1 mAb microstructure with the presence of electrolytes also suggests important non-electrostatic contributions, such as hydrophobic interactions [26]. Fc-fusion proteins are even more likely to undergo conformational changes compared to complete mAbs due to lack of inter- and intra-molecular domain stability. Fast et al. [31] reported rapid aggregation of an Fc-fusion protein, abatacept (Orencia), when pH was lowered from 7.5 to 6.0 at 40° C. Conformational changes and aggregate formation were attributed to the instability of CDR (CTLA-4) and $CH_2$ domains which unfold to form a molten globule-like structure that is prone to aggregation.

Furthermore, the solution conditions to which proteins are exposed in the CEX column can be difficult to determine due to complex ionic equilibrium between the mobile and the stationary phases. As a result, situations may arise where the impact of protein solution properties is convoluted with that of the chromatographic processes in understanding complex column phenomena. For example, it was reported that an unexpected pH drop can occur in CEX during salt elution due to competitive equilibrium between buffer salt ions and $H^+/OH^-$ ions [32-34]. When high salt buffer is introduced in the elution step, the cations in the mobile phase displace the $H^+$ ions in the stationary phase. These released $H^+$ ions then enter into the mobile phase and cause the temporary reduction of pH in the eluate. Extra cautions should be taken for unstable proteins in such transient conditions where the local environment of high salt and low pH, in addition to high intra-pore protein concentration upon elution, can cause protein denaturation and aggregation.

Accordingly, there is a need in the art for improved protein purification methods that can be used to reduce aggregation formation during the protein purification process.

SUMMARY OF THE INVENTION

In certain embodiments, the present invention provides a method of purifying a protein of interest with a reduced level of aggregation formation in cation exchange (CEX) chromatography, comprising: (a) providing a mixture comprising the protein of interest and one or more contaminants; (b) loading the mixture onto a CEX resin coupled with arginine; and (c) eluting the protein of interest from the resin, thereby purifying the protein of interest with a reduced level of aggregation formation in CEX chromatography. For example, the mixture comprises clarified bulk or a cell culture supernatant (e.g., a supernatant from a mammalian, bacterial or fungal cell culture). In a specific example, the mixture is a supernatant from a Chinese Hamster Ovary (CHO) cell culture. To illustrate, the contaminants are selected from host cell proteins, host cell metabolites, host cell constitutive proteins, nucleic acids, endotoxins, viruses, product related contaminants, lipids, media additives and media derivatives. To illustrate, the protein of interest is selected from an antibody (e.g., a monoclonal antibody selected from a human antibody, a humanized antibody, and a chimeric antibody), an antibody fragment, and an Fc fusion.

In certain aspects, the base matrix material of the CEX resin of the present invention is selected from agarose, cellulose, dextran, chitosan, poly(methacrylate), acrylic polymers, and poly(styrene-divinyl-benzene). The CEX resin is prepared using a cation exchange ligand functionality selected from sulfonate, carboxylic, carboxymethyl sulfonic acid, sulfoisobutyl, sulfoethyl, carboxyl, sulphopropyl, sulphonyl, sulphoxyethyl and orthophosphate. In a specific embodiment, the CEX resin coupled with arginine is an arginine-sulphopropyl (Arg-SP) resin (e.g., an arginine-sulphopropyl (Arg-SP) agarose resin).

In certain aspects, before the CEX chromatography step, the mixture is prepared by an affinity chromatography selected from a protein A affinity chromatography and a protein G affinity chromatography. Optionally, the affinity chromatography is a protein A affinity chromatography. In certain aspects, the method of the present invention further comprises one or more additional chromatography matrixes, such as an anion exchange chromatography, a hydrophobic interaction chromatography, and/or a mix-mode chromatography.

In other embodiments, the present invention provides a cation exchange (CEX) resin coupled with arginine. For example, the base-matrix material of the CEX resin is selected from agarose, cellulose, dextran, chitosan, poly (methacrylate), acrylic polymers, and poly(styrene-divinyl-benzene). For example, the CEX resin is prepared using a cation exchange ligand functionality selected from sulfonate, carboxylic, carboxymethyl sulfonic acid, sulfoisobutyl, sulfoethyl, carboxyl, sulphopropyl, sulphonyl, sulphoxyethyl and orthophosphate. In a specific embodiment, the CEX resin coupled with arginine is an arginine-sulphopropyl (Arg-SP) resin such as an arginine-sulphopropyl (Arg-SP) agarose resin.

DETAILED DESCRIPTION OF THE INVENTION

Figure 1A:
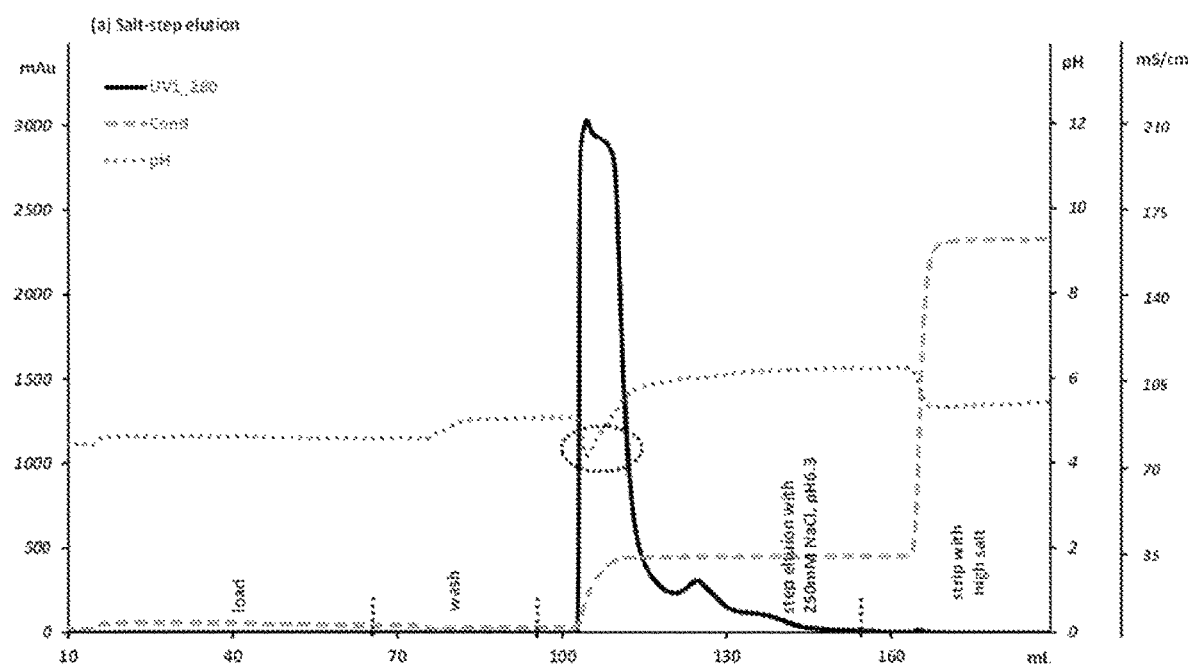
FIG. 1A shows the chromatograms of SP SFF using salt-step elution. The CEX column was loaded at 30 g/L resin at pH 4.5, washed with 50 mM NaAcetate, pH 5.0, and eluted with 50 mM NaAcetate, 250 mM NaCl, pH 6.3 (a) or 50 mM NaAcetate, pH 8.3 (b), respectively.

In certain embodiments, the present invention provides a method of purifying a protein of interest with a reduced level of aggregation formation in cation exchange (CEX) chromatography, comprising: (a) providing a mixture comprising the protein of interest and one or more contaminants; (b) loading the mixture onto a CEX resin coupled with arginine; and (c) eluting the protein of interest from the resin, thereby purifying the protein of interest with a reduced level of aggregation formation in CEX chromatography. In a specific embodiment, the CEX resin coupled with arginine is an arginine-sulphopropyl (Arg-SP) resin, such as an arginine-sulphopropyl (Arg-SP) agarose resin. For example, the mixture comprises clarified bulk or a cell culture supernatant. To illustrate, the protein of interest is selected from an antibody, an antibody fragment, and an Fc fusion. Optionally, before the CEX chromatography step, the mixture is prepared by an affinity chromatography (e.g., a protein A affinity chromatography and a protein G affinity chromatography). Optionally, the method of the present invention further comprises one or more additional chromatography matrixes, such as an anion exchange chromatography, a hydrophobic interaction chromatography, and/or a mix-mode chromatography.

In other embodiments, the present invention provides a cation exchange (CEX) resin coupled with arginine. In a specific embodiment, the CEX resin coupled with arginine is an arginine-sulphopropyl (Arg-SP) resin, such as an arginine-sulphopropyl (Arg-SP) agarose resin.

Definitions

As used herein, the terms "purifying" and "separating" are used interchangeably, and refer to the removal of contaminants from a mixture containing a protein of interest (e.g., an antibody).

As used herein, the term "protein of interest" is used in its broadest sense to include any protein (either natural or recombinant), present in a mixture, for which purification is desired. Such proteins of interest include, without limitation, hormones, growth factors, cytokines, immunoglobulins (e.g., antibodies), immunoglobulin-like domain-containing molecules (e.g., ankyrin or fibronectin domain-containing molecules), and Fc-fusion proteins. The term "Fc-fusion protein", as used herein, is meant to encompass therapeutic proteins comprising an immunoglobulin-derived moiety (i.e., an Fc moiety) and a moiety derived from a second, non-immunoglobulin protein.

As used herein, a "mixture" comprises a protein of interest (for which purification is desired) and one or more contaminant, i.e., impurities. In one embodiment, the mixture is produced from a host cell or organism that expresses the protein of interest (either naturally or recombinantly). Such mixtures include, for example, cell cultures, cell lysates, and clarified bulk (e.g., clarified cell culture supernatant).

As used herein, the term "contaminant" is used in its broadest sense to cover any undesired component or compound within a mixture. In cell cultures, cell lysates or clarified bulk (e.g., cell culture supernatant), contaminants include, for example, host cell nucleic acids (e.g., DNA) and host cell proteins present in a cell culture medium, proteins related to or derived from the protein of interest (e.g., proteolytic fragments) and other product related contaminants (e.g., truncated and aggregated versions of the protein of interest). Host cell contaminant proteins include, without limitation, those naturally or recombinantly-produced by the host cell.

As used herein, "washing" refers to passing an appropriate buffer through or over a cation exchange resin.

As used herein, "eluting" refers to removing a protein of interest (e.g., an antibody) from a cation exchange resin, by altering the pH and/or ionic strength of the buffer surrounding the cation exchange resin such that the buffer competes with the molecule for the charged sites on the ion exchange material.

As used herein, a "cell culture" refers to cells in a liquid medium that produce a protein of interest. The cells can be from any organism including, for example, bacteria, fungus, mammals or plants. Suitable liquid media include, for example, nutrient media and non-nutrient media.

As used herein, the term "clarified bulk" refers to a mixture from which particulate matter (e.g., cells) has been substantially removed. Clarified bulk includes cell culture supernatant, or cell lysate from which cells or cell debris have been substantially removed by, for example, filtration or centrifugation.

The term "antibody" is used in the broadest sense to cover any type of known antibody, including, but is not limited to, monoclonal antibodies (including full length monoclonal antibodies), polyclonal antibodies, monospecific antibodies, multispecific antibodies (e.g., bispecific antibodies), immunoadhesins, antibody-immunoadhesin chimeras, humanized, human, chimeric, single-chain, synthetic, recombinant, hybrid, mutated, grafted, or in vitro generated antibodies. The antibody can be a full-length antibody or an antibody fragment. The antibody may be selected from any of the known antibody isotypes, for example, IgA, IgG, IgD, IgE, IgM. The antibody may be a monomer, dimer, or multimer (e.g., a trimer or pentamer).

An "antibody fragment" includes at least a portion of a full-length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403, 484; 5,571,698; 5,427,908 5,580,717; 5,969,108; 6,172,197; 5,885,793; 6,521,404; 6,544,731; 6,555,313; 6,582,915; and 6,593,081.

Monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody)

in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-Mouse® (Medarex, Inc., Princeton, N.J.) which has a human heavy chain transgene and a human light chain transchromosome (see WO 02/43478), Xenomouse® (Abgenix, Inc., Fremont Calif.; described in, e.g., U.S. Pat. Nos. 5,939,598; 6,075,181; 6,114,598; 6,150,584 and 6,162,963 to Kucherlapati et al.), and HuMAb-Mouse® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994)*J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange (CEX), anion exchange, and mixed mode chromatography.

A "cation exchange resin" or "CEX resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate. Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies); a sulfoethyl based group (e.g., Fractogel SE, from EMD, Poros S-10 and S-20 from Thermo Scientific); a sulphopropyl based group (e.g., TSK Gel SP 5PW and SP-5PW-HR from Tosoh, Poros HS-20 and HS 50 from Thermo Scientific); a sulfoisobutyl based group (e.g., Fractogel EMD $SO_3^-$ from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufine C500 and C200 from EMD-Millipore, CM52, CM32, CM23 and Express—Ion C from Whatman, Toyopearl CM-650S, CM-650M and CM-650C from Tosoh); sulfonic and carboxylic acid based groups (e.g., BAKERBOND Carboxy-Sulfon from J. T. Baker); a carboxylic acid based group (e.g., WP CBX from J. T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO— from EMD); a sulfonic acid based group (e. g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., P11 from Whatman).

Mixtures Containing a Protein of Interest

The methods of the invention can be applied to purify one or more protein(s) of interest from any mixture containing the protein(s). In one embodiment, the mixture is obtained from or produced by living cells that express the protein to be purified (e.g., naturally or by genetic engineering). Methods of genetically engineering cells to produce proteins are well known in the art. See e.g., Ausabel et al., eds. (1990), Current Protocols in Molecular Biology (Wiley, New York) and U.S. Pat. Nos. 5,534,615 and 4,816,567, each of which is specifically incorporated herein by reference. Such methods include introducing nucleic acids that encode and allow expression of the protein into living host cells. These host cells can be bacterial cells, fungal cells, or, preferably, animal cells grown in culture. Bacterial host cells include, but are not limited to E. coli cells. Examples of suitable E. coli strains include: HB101, DH5α, GM2929, JM109, KW251, NM538, NM539, and any E. coli strain that fails to cleave foreign DNA. Fungal host cells that can be used include, but are not limited to, Saccharomyces cerevisiae, Pichia pastoris and Aspergillus cells. A few examples of animal cell lines that can be used are CHO, VERO, DXB11, BHK, HeLa, Cos, MDCK, 293, 3T3, NS0 and WI138. New animal cell lines can be established using methods well know by those skilled in the art (e.g., by transformation, viral infection, and/or selection). In other embodiments, the protein of interest (e.g., an antibody) is produced in a CHO cell (see, e.g., WO 94/11026). Various types of CHO cells are known in the art, e.g., CHO-K1, CHO-DG44, CHO-DXB11, CHO/dhfr⁻ and CHO-S.

Preparation of mixtures initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

In one embodiment, cells or cellular debris are removed from the mixture, for example, to prepare clarified bulk. The methods of the invention can employ any suitable methodology to remove cells or cellular debris, including, centrifugation, tangential flow filtration or depth filtration.

Protein Purification

The methods of the invention provide improved techniques for CEX purification of a protein of interest (e.g., an antibody or an Fc fusion protein) from a mixture. These methods generally comprise the steps of: (a) providing a mixture comprising the protein of interest and one or more contaminants; (b) loading the mixture onto a CEX resin coupled with arginine; and (b) eluting the protein of interest from the resin, thereby purifying the protein of interest with a reduced level of aggregation formation in a CEX chromatography. In a specific embodiment, the CEX resin coupled with arginine is an arginine-sulphopropyl (Arg-SP) agarose resin. However, the skilled artisan will appreciate that additional purification can be performed before, after or in between the steps of the aforementioned method. Use of the CEX resin coupled with arginine results in reduced aggregation formation of the protein of interest, compared to use of the CEX resin which is not coupled with arginine.

Binding of the protein of interest (e.g., an antibody) to a cation exchange resin can be performed at any pH below the pI of the most acidic isoform of the protein to be purified. In particular embodiments, the protein of interest is bound to the resin between about pH 4 and about pH 8 (e.g., about pH 4, 4.5, 5, 5.5, 6, 6.5, 7, 7.5, and 8). In one exemplified embodiment, the protein of interest is bound to the resin at about pH 6.2. In another exemplified embodiment, the protein of interest is bound to the resin at about pH 4.5.

Once the protein of interest is bound to the cation exchange resin, contaminants (e.g., HCP) are removed by washing the resin with a buffer. The optimal pH for washing the resin can be determined empirically for each protein of interest by monitoring the purity and yield of the purified protein. The wash buffer can be augmented with detergents or surfactants (e.g., polysorbate) to further remove contaminants, e.g., DNA and endotoxin contaminants.

After washing the cation exchange resin, the protein of interest is eluted using a buffer. In general, the elution is facilitated by increasing the pH of the elution buffer or by increasing the ionic strength of the elution buffer relative to the binding buffer, for example, by the addition of a salt (e.g., sodium chloride) to the elution buffer. In addition, a polyether (e.g., polyethylene glycol) can be added to the elution buffer to reduce protein aggregation and the formation of higher molecular weight species.

Preparation of CEX Resin Coupled with Arginine

In certain embodiments, the present invention provides CEX resin which is coupled with arginine. Coupling CEX resin with arginine can be performed in various ways via amine-reactive chemistries, for example, but not limited to, NHS ester, imidoester, pentafluorophenyl ester, hydroxymethyl phosphine, etc.

As illustrated in the working example below, SP agarose resin can be prepared by coupling the primary amine group of 3-amino-1-propanesulfonic acid with NETS-activated agarose beads. Arg-SP agarose resin can be prepared by sequentially coupling L-arginine and 3-amino-1-propanesulfonic acid to the NETS-activated agarose beads. NETS-activated agarose slurry is first thoroughly washed with DI water to remove the acetone storage solution, and subsequently washed with a coupling buffer of 0.1 M sodium phosphate, 0.15 M NaCl, pH 7.2 using a filter flask with 0.2 μm filter paper. To prepare SP agarose resin, the agarose beads can be then mixed with 300 mM 3-amino-1-propanesulfonic acid at a volume ratio of 1:2 for 2 h at room temperature. To prepare Arg-SP agarose resin, the agarose beads are first mixed with 300 mM L-arginine for 5 min, washed with the coupling buffer, and then mixed with 300 mM 3-amino-1-propanesulfonic acid for another 2 h at room temperature. Approximately 80% of the coupling reactions occurs in first 0.5 h. The ligand-immobilized agarose beads are extensively washed with the coupling buffer before adding 1 M ethanolamine, pH 7.4 solution to cap the un-reacted NHS functional groups. Finally, the functionalized agarose beads are washed again with the coupling buffer for column packing.

The present disclosure is further illustrated by the following examples, which should not be construed as further limiting. The contents of all figures and all references, patents and published patent applications cited throughout this application are expressly incorporated herein by reference in their entireties.

EXAMPLE 1

Insights in Understanding Aggregate Formation and Dissociation in Cation Exchange Chromatography for a Structurally Unstable Fc-Fusion Protein Materials and Methods 1. Chemicals, Resins and Protein All chemicals were obtained from J. T. Baker (Phillipsburg, N.J., USA) unless otherwise noted. 3-Amino-1-propanesulfonic acid (3APS) and ethanolamine were purchased from Sigma-Aldrich (St. Louis, Mo., USA). SP Sepharose Fast Flow (SP SFF) and CM Sepharose Fast Flow (CM SFF) resins were obtained from GE Healthcare Sciences (Uppsala, Sweden). Poros XS resin and N-hydroxysuccinimide (NHS)-activated agarose slurry were purchased from Life Technologies (Waltham, Mass., USA). UNOsphere Rapid S and gel filtration standard were purchased from Bio-Rad (Philadelphia, Pa.). The Fc-fusion protein used in this work was expressed in Chinese Hamster Ovary (CHO) cells and produced at Bristol-Myers Squibb, Co. The overall molecular weight of this Fc-fusion protein is 78 kDa. The experimental pI (isoelectric point) is 7.2 determined by Zeta potential measurement. As mentioned earlier, there is no disulfide bond in the hinge region and elsewhere between the two single chains for this Fc-fusion protein. Protein load materials used in this study were obtained by buffer exchanging Protein A purified pool into target solution conditions.

2. Chromatography Instrumentation and Methods

All chromatography runs were performed using a GE Healthcare ÄKTA AVANT system installed with Unicorn software version 6.3 (Piscataway, N.Y., USA). SP SFF, CM SFF and Poros XS resins were packed into C10/10 columns (1.0 cm I.D×10 cm bed height) purchased from GE Healthcare (Piscataway, N.Y., USA). The packed and conditioned column was equilibrated with 5 column volumes (CV) of 50 mM NaAcetate, pH 4.0-5.5, followed by protein loading at corresponding pH using a 6-min residence time (unless otherwise noted). The column was then washed with 3 CV of 50 mM NaAcetate, pH 5.0. The bound Fc-fusion protein was eluted with either 50 mM NaAcetate, 250 mM NaCl, pH 6.3 or 50 mM NaAcetate, pH 8.3, with the eluate collected in fractions between an absorbance of 0.15 OD on each side of the peak to achieve maximum product recovery. It should be noted that the elution pH conditions (pH 6.3, 8.3) are outside normal acetate buffering capacity. They were selected here mainly to simplify the solution compositions without changing buffer matrix (e.g., MES or phosphate) or introducing additional ion types. The primary focus of this work was to gain a mechanistic understanding of aggregation phenomena associated with CEX step, therefore a sophisticate peak-cutting strategy was not utilized to achieve monomer purification. The column was regenerated with 3 CV of 2 M NaCl, sanitized with 3 CV of 1 M NaOH, and finally stored in 0.1 M NaOH after each run. Protein concentration was measured using a NanoDrop 2000 purchased from Thermo Fisher Scientific (Wilmington, Del., USA). All runs were performed at room temperature.

3. SEC Method for Aggregate Analysis

Analytical SEC was carried out using a TSKgel G3000SWXL column from Tosoh Bioscience (King of Prussia, Pa., USA) installed on a Waters HPLC system from Waters Corporation (Milford, Mass., USA). The method used 100 mM sodium phosphate, 100 mM sodium sulfate, pH 6.8, at a flow rate of 1 mL/min, with a constant total injected protein mass of 100 μg. The eluted protein was monitored by UV 280 nm.

4. Sypro Orange Dye Experiment

SP SFF, CM SFF and Poros XS resins were buffer exchanged into 25 mM NaAcetate, pH 5.0 buffer and adjusted to 50% (v/v) gravity-settled slurry. For dye-containing samples, 400 μL resin slurry was mixed with 98.5 μL of 25 mM NaAcetate, pH 5.0 buffer and 1.5 μL of Sypro Orange dye (5000×) purchased from Invitrogen (Paisley, Scotland, U.K.). For the non-labeling control samples, 400 μL resin slurry was mixed with 100 μL of 25 mM NaAcetate, pH 5.0 buffer. All the samples were inverted on a roller mixer for 5 min at 180 rpm and then gravity settled before taking pictures.

5. Differential Scanning Fluorimetry (DSF) Study

The resins, SP SFF and CM SFF, were buffer exchanged into corresponding buffers (50 mM NaAcetate, pH 4.0-5.5) and adjusted to 50% (v/v) gravity-settled slurry. The experiment was performed using a 7500 Real-Time PCR (RT-PCR) system (software version 1.4.1) from Applied Biosystems (Warrington, Cheshire, U.K.). Briefly, resin (final 10% v/v), protein (final 1 g/L), Sypro Orange dye (final 15×), and buffer at corresponding pH were mixed in a pre-calculated ratio and added to a fast optical 96 well reaction plate (Applied Biosystems) to a final volume of 20 μL/well, with each condition prepared in duplicates. After sealing with optical adhesive film purchased from Applied Biosystems, the plate was directly analyzed in the RT-PCR. The heating cycle comprised a 4° C. pre-cooling step for 2 min and a subsequent gradient from 4° C. to 53° C. in 99 steps with each ramp of 0.5° C. for 30 sec. Data was collected using the calibration settings ($\lambda_{ex}$ 490 nm; $\lambda_{em}$ 580 nm) for detecting Sypro Orange dye, and analyzed by fitting the fluorescence data to a modified Clarke and Fersht equation [35].

$$I(T) = \frac{\alpha_F + \beta_F T + (\alpha_A + \beta_A T) \cdot e^{m(T-T_m)}}{1 + e^{m(T-T_m)}}$$

Where I(T) is the fluorescence intensity; T is actual temperature of each fluorescence data point; $T_m$ is the melting temperature; $\alpha_F$ and $\beta_F$ are the intercept and slope of the baseline for the folded state respectively; $\alpha_A$ and $\beta_A$ are the intercept and slope, respectively, for the fluorescence quenching step at high temperature; m is an exponential factor associated with the slope of the transition at the apparent melting temperature. Values of $\alpha_F$, $\beta_F$, $\alpha_A$, $\beta A$, m and $T_m$ were obtained by using a least squares method to fit the DSF data.

6. In-House Resin Preparation

SP agarose resin was prepared by coupling the primary amine group of 3-amino-1-propanesulfonic acid with NETS-activated agarose beads. Arg-SP agarose resin was prepared by sequentially coupling L-arginine and 3-amino-1-propanesulfonic acid to the NETS-activated agarose beads. NETS-activated agarose slurry was first thoroughly washed with DI water to remove the acetone storage solution, and subsequently washed with a coupling buffer of 0.1 M sodium phosphate, 0.15 M NaCl, pH 7.2 using a filter flask with 0.2 μm filter paper. To prepare SP agarose resin, the agarose beads were then mixed with 300 mM 3-amino-1-propanesulfonic acid at a volume ratio of 1:2 for 2 h at room temperature. To prepare Arg-SP agarose resin, the agarose beads were first mixed with 300 mM L-arginine for 5 min, washed with the coupling buffer, and then mixed with 300 mM 3-amino-1-propanesulfonic acid for another 2 h at room temperature. Approximately 80% of the coupling reactions occurs in first 0.5 h according to vendor provided protocol. The ligand-immobilized agarose beads were extensively washed with the coupling buffer before adding 1 M ethanolamine, pH 7.4 solution to cap the un-reacted NETS functional groups. Finally, the functionalized agarose beads were washed again with the coupling buffer for column packing. The Arg-SP agarose resin prepared in this work was packed into a 5 mm i.d. AP Mini Glass Column (Waters Corporation, Milford, Mass., USA) with a bed height of approximately 5 cm.

7. Modeling Methodology

The protein 3D structure was obtained using homology modeling within the BIOVIA Discovery Studio software [36]. Based on protein structure, the spatial-aggregation-propensity (SAP) model was used to determine the aggregation-prone hydrophobic regions, using the homology-modeled structure within Discovery Studio. The SAP value for each atom in the protein is defined as follows [37], $$\left( \begin{array}{c} \text{Spatial} - \text{aggregation} - \\ \text{propensity (SAP)} \end{array} \right)_{atom\ i} = \sum_{\substack{\text{Residues with at least} \\ \text{one side chain atom} \\ \text{within R from atom i}}} \left( \frac{SAA \text{ of side chain atoms}}{SAA \text{ of side chain atoms}} \times \text{Residue Hydrophobicity} \right)$$ [2]

Here, SAA (solvent accessible area) of side chain atoms within radius (R) of 10 Å is computed, where SAA of side chain of fully exposed residues is obtained by calculating the SAA of side chains of the middle residue in the fully extended conformation of tripeptide. Residue hydrophobicity is obtained from the hydrophobicity scale [38] which is normalized such that glycine has a hydrophobicity of zero. Therefore, those amino acids that are more hydrophobic than glycine are positive and that are less hydrophobic than glycine are negative on the hydrophobic scale. The SAP for a residue is obtained by averaging the SAP of all its constituent atoms. Protein SAP score, which gives the overall hydrophobicity of the protein surface, is obtained by summing up the SAP values for all the residues with positive SAP scores.

The protein charge at different pH conditions is calculated based on the protein ionization protocol in the Discovery Studio software. The charge is based on predicting the $pK_{1/2}$ and titration curves for each one of the titratable amino acid residues within the protein structure. The electrostatic potential is calculated using the Delphi program within Discovery Studio. The Delphi program solves the Poisson-Boltzmann equation on a cubical lattice using the finite-difference technique. The CHARMM fully atomistic force field [39] is used in these charge and potential calculations. The electrostatic potential is visualized by coloring the molecular surface with the potentials calculated. The mean residue potentials are calculated by averaging the values of electrostatic potentials at its constituent atoms.

Results and Discussion

1. Aggregation Behaviors of the Fc-Fusion Protein in CEX

Figure 1B:
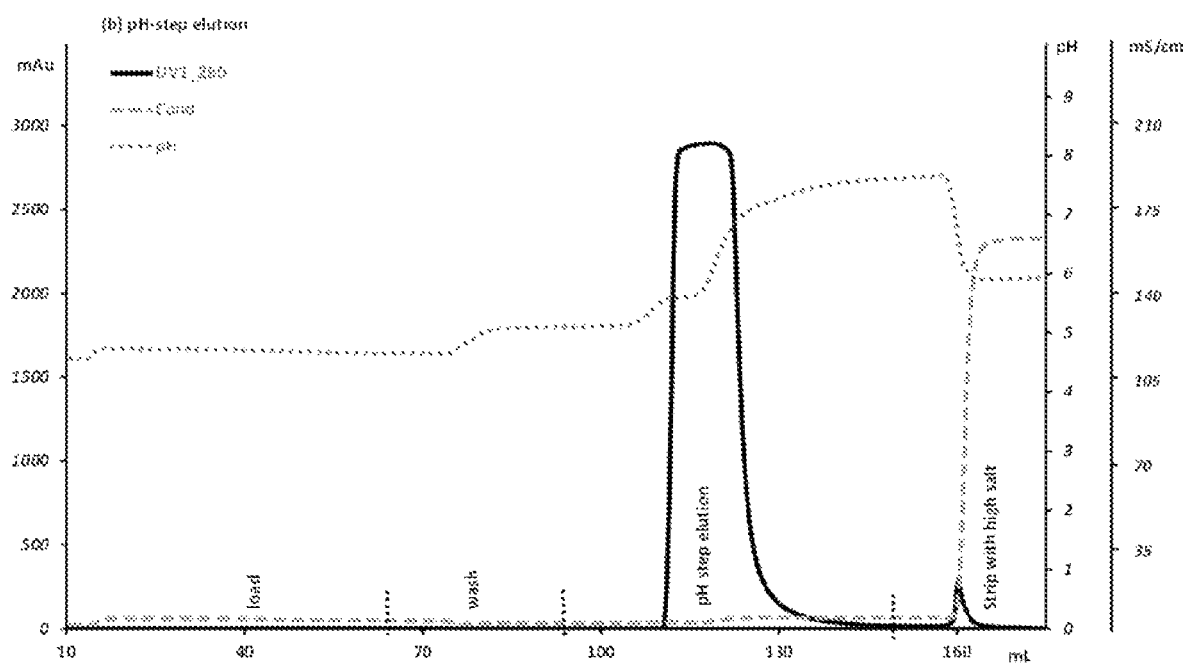
FIG. 1B shows the chromatograms of SP SFF using pH-step elution. The CEX column was loaded at 30 g/L resin at pH 4.5, washed with 50 mM NaAcetate, pH 5.0, and eluted with 50 mM NaAcetate, 250 mM NaCl, pH 6.3 (a) or 50 mM NaAcetate, pH 8.3 (b), respectively.

A multi-peak elution profile (FIG. 1a) was observed on a SP SFF column during salt-step elution using 50 mM NaAcetate, 250 mM NaCl, pH 6.3. The eluate aggregate level (8.6%) based on SEC analysis was much higher than that for the load material (1.5%), and indicated a significant aggregate formation during the CEX step. The tracers in FIG. 1a showed a temporary pH drop (to <pH 4.5) during salt transition which occurred concurrently with the elution front, leading to a temporary low pH and high salt environment. Elution buffer of 50 mM NaAcetate, 250 mM NaCl, pH 5.6 showed similar pH transition phenomenon as acetate at pH 6.3. Acetate at pH 6.3 was used in the salt-step elution to maximize protein recovery for better quantification of the aggregates formed. Similar pH transition phenomenon during salt-step elution has been reported in other studies [32-34]. Low pH and high salt were found to cause aggregation and precipitation based on an in-solution protein stability study. A separate study with elution fractionations (not shown) also confirmed that the late eluting peak contains higher aggregate level, similar to a previous report [12]. On the contrary, a pH-step elution using 50 mM NaAcetate, pH 8.3 resulted in single-peak elution and smooth pH transition (FIG. 1b). Nevertheless, major aggregate formation was also observed in the eluate (6.1%). The single-peak elution profile indicates that the monomer and the aggregates formed during the pH-step elution had similar elution properties. Based on the protein in-solution stability (at room temperature for 24 hours) evaluated in a separate study (data not shown), the protein was stable in solution between pH 4.0-8.0 at low salt concentrations, and no aggregate generation was observed in the conditions examined. This study provided sufficient evidence to exclude protein solution property as the root cause for the aggregation phenomenon observed in the pH-step elution study.

Figure 2:
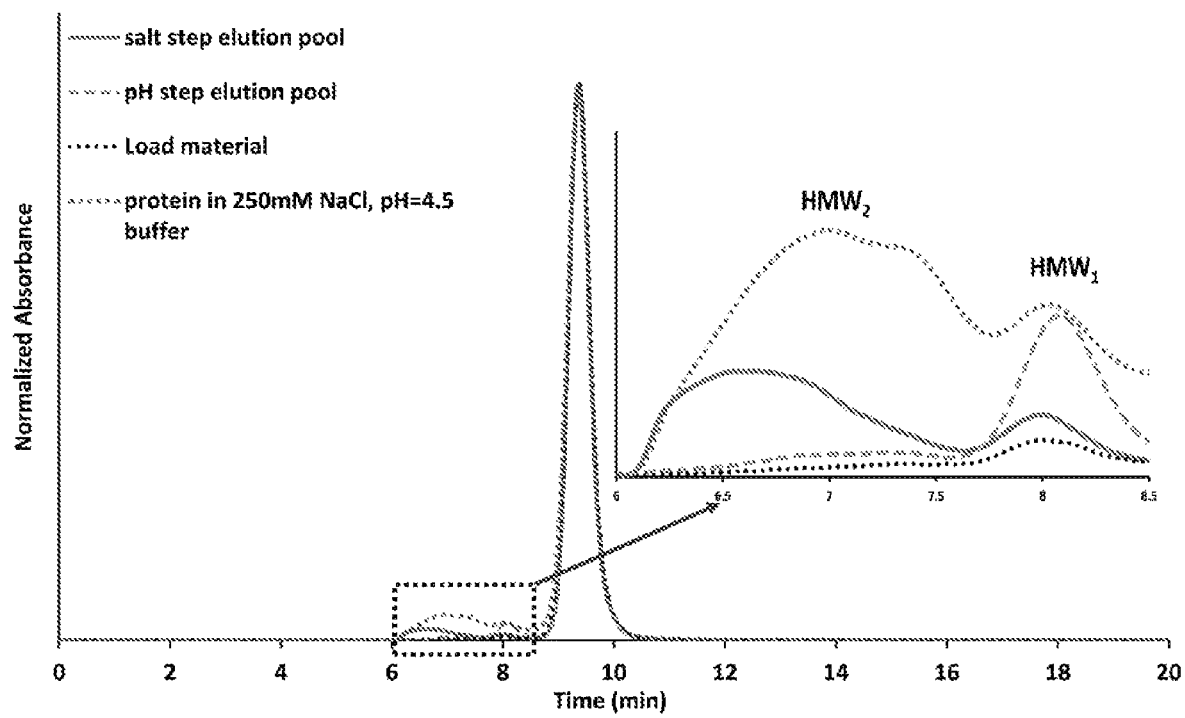
FIG. 2 shows the SEC profile of the salt-step and pH-step eluate (on SP SFF), load material (in 50 mM NaAcetate, pH 4.5 buffer), and a control solution sample in 50 mM NaAcetate, 250 mM NaCl, pH 4.5 buffer.

To better understand the aggregate species formed during the two different elution conditions, SEC profiles of the salt-step and pH-step elution pools were compared with that of the load material (in 50 mM NaAcetate at pH 4.5) and a protein solution prepared using 50 mM NaAcetate, 250 mM NaCl, at pH 4.5. The buffer condition of the protein solution sample was selected to mimic that in the buffer transition region inside the column upon elution (FIG. 1a). Considering that the protein concentration and solution condition at the peak maximum varied as the elution progressed in the column and that the protein mass in the buffer transition region is only a fraction of the total eluted protein, it is practically impossible to identify the condition for the solution sample to be truly comparable to the elution samples. Therefore, the protein solution sample can only provide a semi-quantitative comparison of the condition that was experienced during actual CEX elution. Two distinct peaks were observed in the SEC profile as shown in FIG. 2. Comparing the retention time of these two peak with the chromatogram of Bio-Rad's gel filtration standard suggests that $HMW_1$ and $HMW_2$ are approximately corresponding to dimer and oligomer species, respectively. Oligomer species were prominent in the solution sample, which was held for a period (≤4 hours) equivalent to the duration of the CEX step (FIG. 2) prior to SEC analysis. A similar SEC profile was also observed in the salt-step eluate, suggesting that the temporary low pH and high salt environment upon elution may also cause protein aggregation and generate similar HMW species. The lower aggregate levels in the salt-step eluate was likely due to the slightly lower salt concentration of the eluate in the buffer transition region, as indicated in FIG. 1a. The majority of the aggregates formed in pH-step elution were dimer, which is different from the aggregates formed in the low pH and high salt condition during salt-step elution. As the pH elution did not create an unfavorable solution environment for the protein, the increased aggregate level was most probably the result of protein-resin interactions in CEX.

Figure 9:
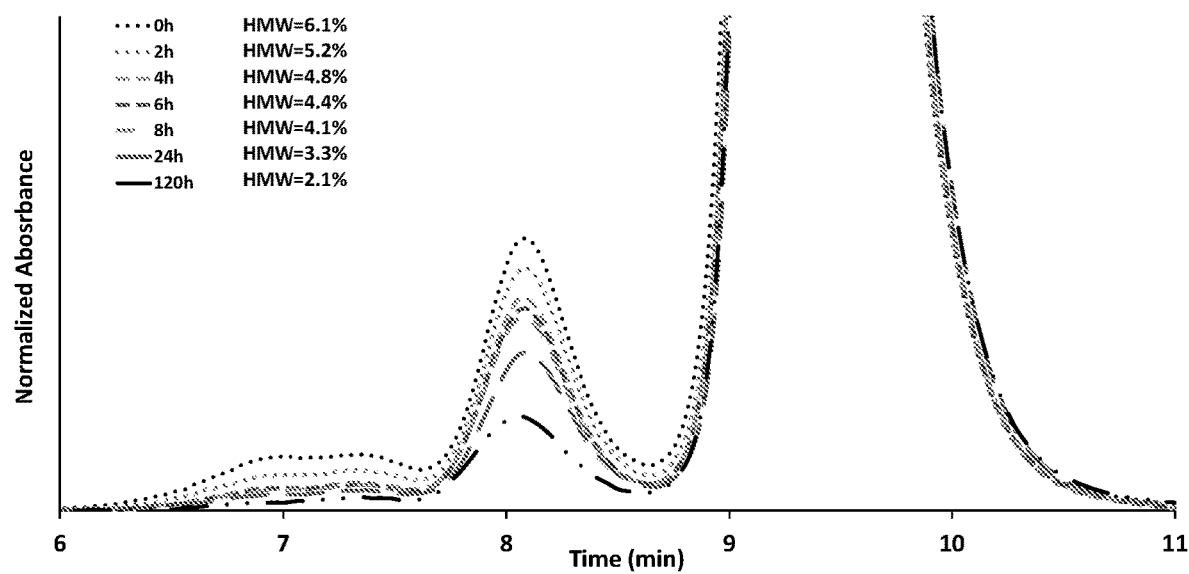
FIG. 9 shows the SEC of SP SFF elution pool (30 g/L resin loading at pH 4.5) at different time points. The pH-step eluate was assayed after 0, 2, 4, 6, 8, 24 and 120 h of incubation at 4° C. upon elution. The aggregate level of the load material was 1.5%.

The pH-step elution was used to evaluate the impact of the protein-resin interactions on the properties of the aggregates formed during the CEX step, because this mode of elution can effectively avoid the solution conditions in which the protein is unstable (e.g., low pH and high salt). Using this approach, the stability of the aggregates in the CEX eluate was studied through periodic SEC analysis for samples held at 4° C. As shown in FIG. 9, the magnitude of the aggregate peak decreased with increasing hold time, suggesting the reversible nature of some aggregate species formed during the CEX step for SP SFF. The eluate aggregate levels decreased from 6.1% to 4.1% in the first 8 hours upon elution and continued to decrease to 2.1% after 5 days. The results suggest that the aggregate dissociation kinetics can affect the level of the eluate aggregate content depending virtually on sample hold time. Therefore, a mechanistic understanding of the contributing factors for the aggregate formation and aggregation reversibility in CEX was particularly important to the development of robust and high-yield CEX purification processes.

2. Proposed Hypothesis

Different from other reported studies [16-18], the aggregate formation required no excessive hold time for the bound protein, and the eluate aggregate levels can be linked to a time-dependent self-dissociation process. The phenomenon observed here suggested a complex aggregation mechanism, giving rise to the hypothesis that the aggregates formed during CEX were likely due to temporary favorable protein-protein interactions between those molecules possessing reversible conformational changes. Notably, aggregate dissociation appeared to be a kinetically-driven process during which the native conformation was gradually regained within a timescale up to several days.

Figure 3:
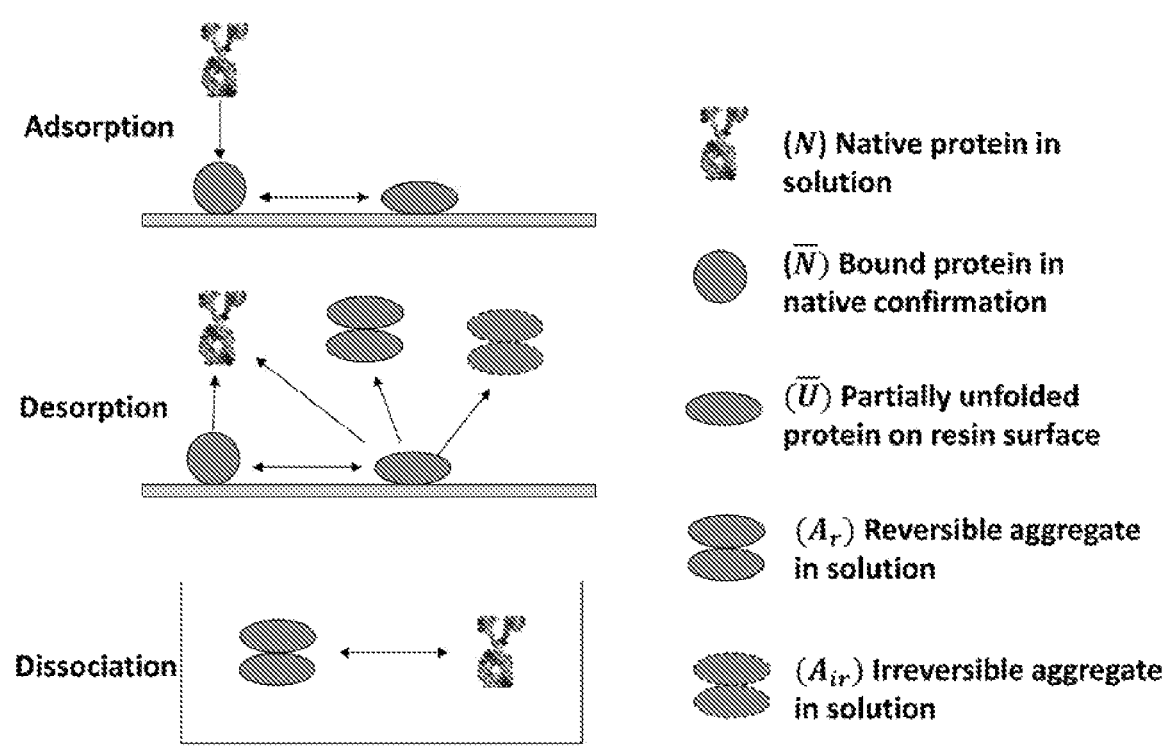
FIG. 3 shows the proposed mechanism of aggregation and dissociation processes.

A schematic representation of the proposed hypothesis is shown in FIG. 3. The hypothesis describes a simple two-step aggregation process during CEX adsorption and desorption as well as an aggregate dissociation process in the CEX eluate. According to the proposed aggregation mechanism, the aggregate level ($A_{ir}+A_r$) in the CEX eluate is the result of two contributing factors: the conformational changes of bound protein and the concentration of these partially unfolded molecules ($\overline{U}$) upon desorption. The two factors together determine the property ($A_{ir}+A_r$) and quantity of the aggregates detected in the CEX eluate. Generally, high degree of conformational changes in $\overline{U}$ and high concentration of $\overline{U}$ will lead to high probability that these unfolded molecules encounter each other and consequently form aggregates, resulting in high eluate aggregate levels. Aggregate formation is mainly due to pairwise and higher order intermolecular interactions for molecules with structural perturbations where protein electrostatic complementarities and varied hydrophobicity may facilitate non-native aggregation [40]. Therefore, not all partially unfolded molecules would be involved in those molecular collisions which ultimately lead to aggregation, especially at low concentration of $\overline{U}$. Depending on the structural changes, some aggregates can be reversible ($A_r$) and ultimately revert to native protein (N) if given sufficient time to reach thermodynamic equilibrium.

3. Mechanistic Studies

1) Effect of Column Loading

Figure 4:
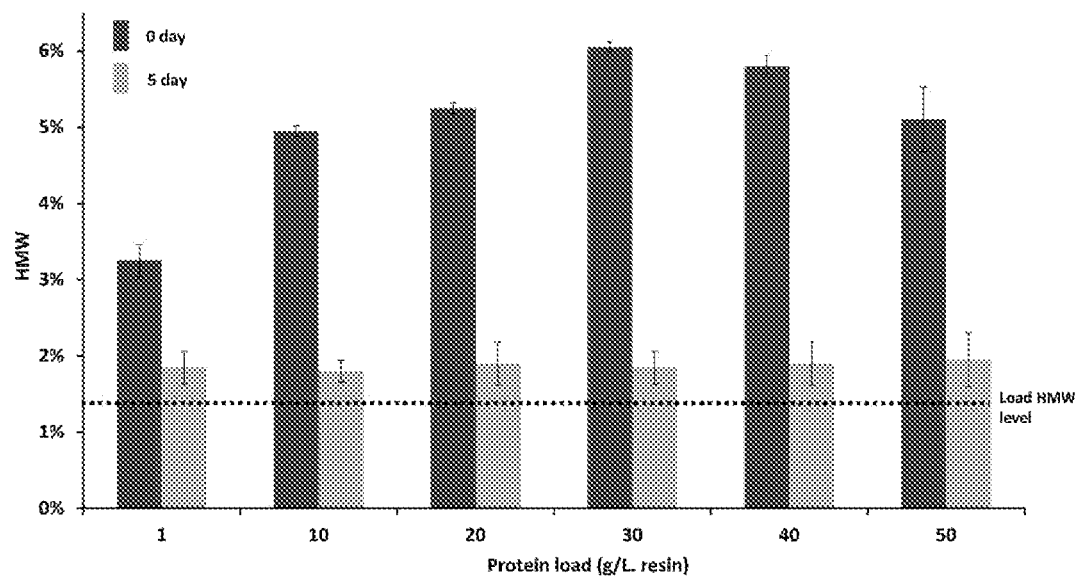
FIG. 4 shows the column loading effect on eluate aggregate levels for SP SFF. SEC test was performed immediately upon pH-step elution (t=0 d) and after 5 days of incubation at 4° C. (t=5 d).

The impact of column loading on the aggregate level in SP SFF eluate was studied. All eluate samples were assayed for SEC immediately upon elution and again after 5 days (storage at 4° C.). The eluate aggregate levels at t=0 d varied significantly within a relatively wide range of column loading (1-50 g/L resin). The dynamic binding capacity of SP SFF is greater than 50 g/L resin. The SEC results are directly compared here in different loading conditions, because all experiments had very high overall product recovery (≥98%). As shown in FIG. 4, the eluate aggregate levels first increased and then slightly decreased, with a maximum aggregate level achieved at approximately 30 g/L resin. Ultimately, all the eluate samples showed practically the same aggregate level after 5 days (t=5 d). Results suggest the impact of column loading on the initial aggregate levels, whereas the amount of the irreversible aggregates in the SP SFF eluate appeared essentially independent of the loading condition in the specific conditions tested. The nonlinear correlation between column loading and eluate aggregate levels (at t=0 d) can be qualitatively understood using the framework of the proposed mechanism by linking protein conformational changes ($\overline{U}$) during adsorption and the concentration of $\overline{U}$ upon desorption. Column loading affects the concentration of $\overline{U}$ upon desorption and the probability that these aggregation-prone protein molecules encounter to form aggregates. The relatively low aggregate level seen in the eluate at low loading was mainly due to the low concentration of $\overline{U}$ during elution, considering the impact of loading on the probability of aggregate formation. In addition, the concave downward trend in FIG. 4 seems to suggest an influence of column loading on the degree of conformational changes of $\overline{U}$, where higher loading may cause reduced protein conformational changes owing probably to steric hindrance and repulsive protein-protein interactions. Conformational changes in $\overline{U}$ usually leads to the exposure of protein hydrophobic surface areas [41] and to energetically favorable condition for protein aggregation [42]. The decreasing level of conformational changes of $\overline{U}$ and increasing level of $\overline{U}$ concentration resulted in the nonlinear pattern observed in FIG. 4, where maximum elution pool HMW was achieved at intermediate loading levels.

2) Effect of Load pH

Figure 10:
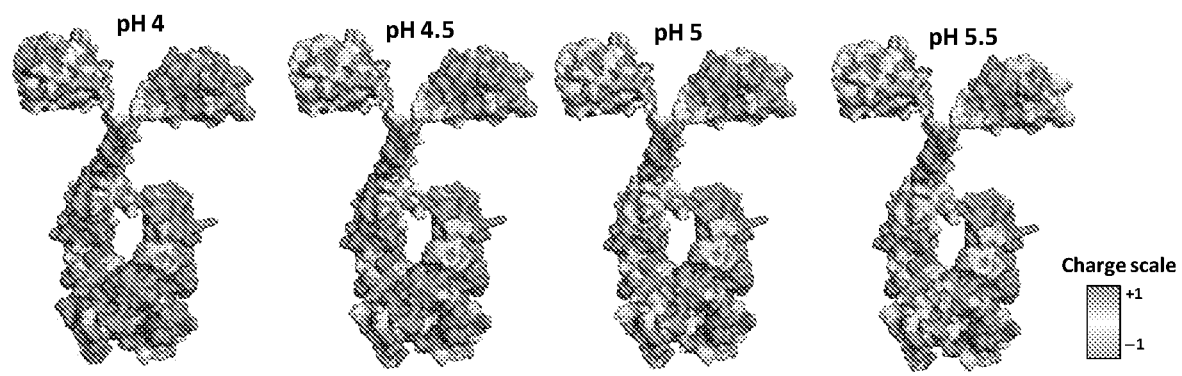
FIG. 10 shows the charge modeling at different pH performed by calculating the electrostatic potential on the surface; negative patches on the surface increase with increasing pH.
Figure 11:
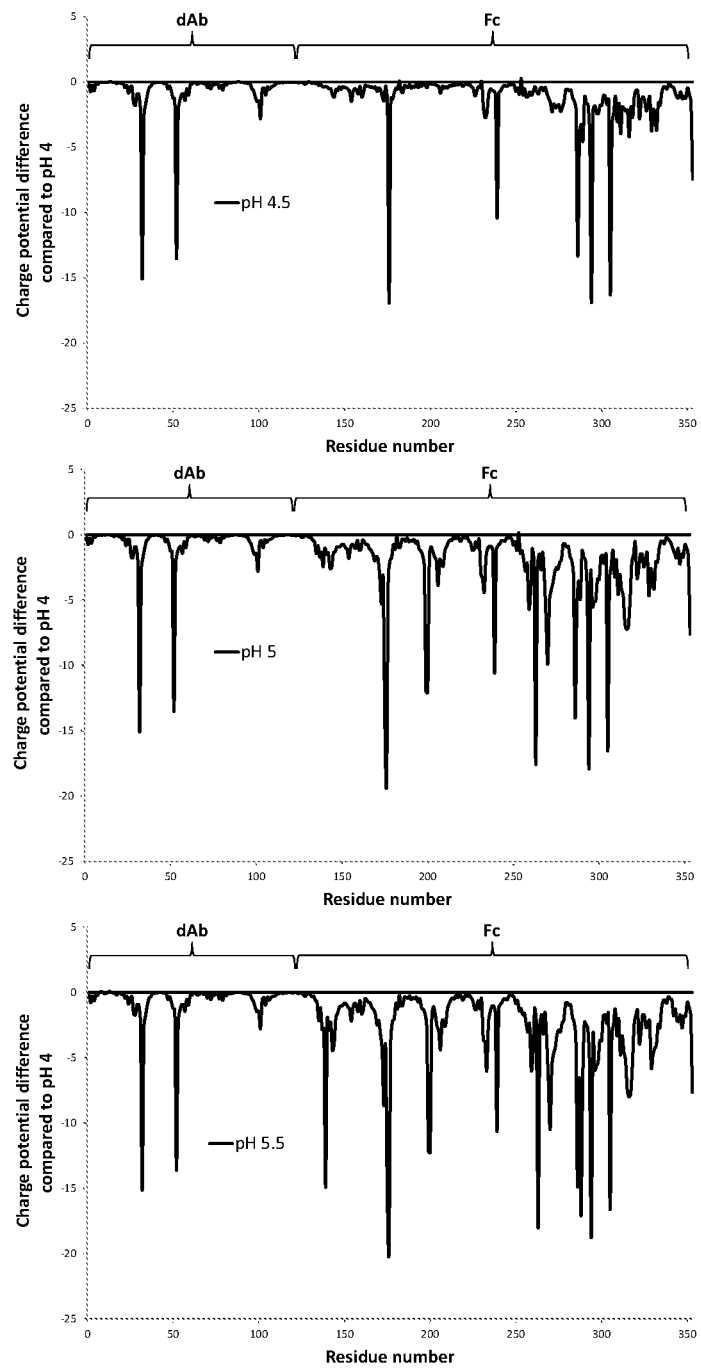
FIG. 11 shows the calculated protein charge potential change compared to values at pH 4 at each residue.

A series of experiments was performed on SP SFF to evaluate the effect of load pH (from 4.0 to 5.5) on the eluate aggregate levels. The load conductivity in different pH conditions varied only within a very small range (2.0-2.5 mS/cm). Table 1 shows that the eluate aggregate levels decreased significantly with increasing load pH, a trend consistent with the overall attractive protein-resin interactions. The electrostatic potential of the protein was calculated using the homology modeling tool described in the methods section to illustrate the charge distribution under different pH conditions. The charge modeling (FIG. 10) indicates that protein surface, especially in the CDR and Fc regions, exhibits more negatively charged patches with increasing pH. These negative surface areas on the protein can create a repulsive environment when interacting with the anionic ligand on the resin, reducing the overall binding strength and protein conformational changes. Furthermore, the charge potential change in FIG. 11 clearly show the locations where the charge potential of the amino acid residues experiences dramatic changes upon a small pH change. Chang and Lenhoff reported [43] that protein-resin interactions can be largely determined by a small number of amino acid residues in the protein structure, which may help explain the impact of the load pH condition on preserving conformational integrity of the bound protein and consequently on reducing the eluate aggregate levels. Chaudhri et. al. [44] used coarse-grained computational models and confirmed that the mAb-mAb association propensity can be significantly different in mutants that differ in only a few amino acids. Identifying the specific amino acid residues that are of particular importance to protein structural stability in CEX can aid in engineering aggregation-resistant molecules [45] through making biologically unimportant changes in protein primary sequence [46]. Apparently, rational design of manufacturing-friendly biologic molecules requires additional modeling efforts to account for the impact of protein-protein and protein-resin interactions on potential protein conformational changes, which is outside the scope of this work.

TABLE 1

Effect of load pH on eluate aggregate level (pH-step elution). The SP SFF column was loaded at 30 g/L resin at different pH conditions. SEC analysis was performed immediately upon elution.

| Load pH | Eluate Aggregate Level |
|---|---|
| pH = 4 | 7.9% |
| pH = 4.5 | 6.1% |
| pH = 5 | 4.0% |
| pH = 5.5 | 3.3% |

Figure 12:
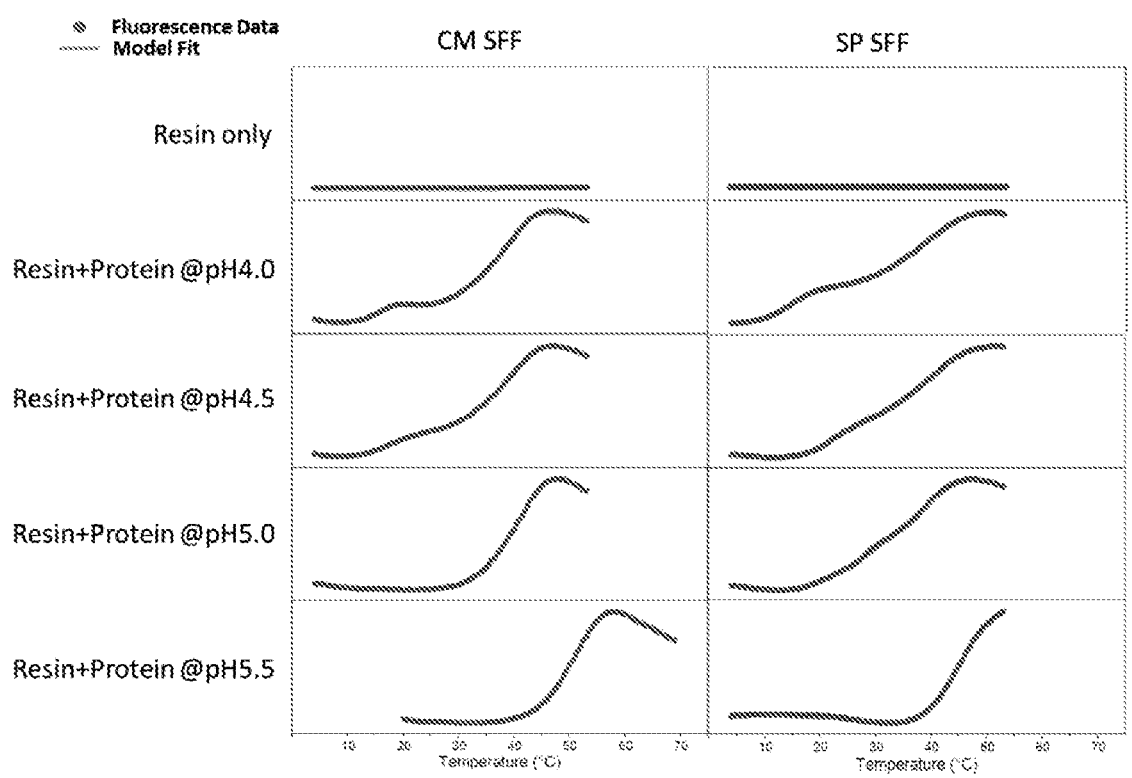
FIG. 12 shows the DSF results for SP SFF, CM SFF, and bound protein in different pH conditions.

As an orthogonal experimental tool, DSF was used to further study the presence and severity of protein conformational changes, and to correlate CEX conditions to eluate aggregate levels. The DSF study was carried out using Sypro Orange dye, a member of merocyamine dye which can activate fluorescence when bound to the hydrophobic surface of studied subjects (e.g., proteins) [47-49]. The DSF results for protein bound with CM and SP Sepharose at different pH was shown in FIG. 12. The stability curves recording the fluorescence of the prepared samples while gradually increasing the temperature were fitted to Eq. 1 to estimate the melting temperature ($T_m$). As $T_m$ the thermal stability of protein conformational integrity, it is used here as a surrogate indicator for protein conformational stability in the solution conditions examined.

Figure 13:
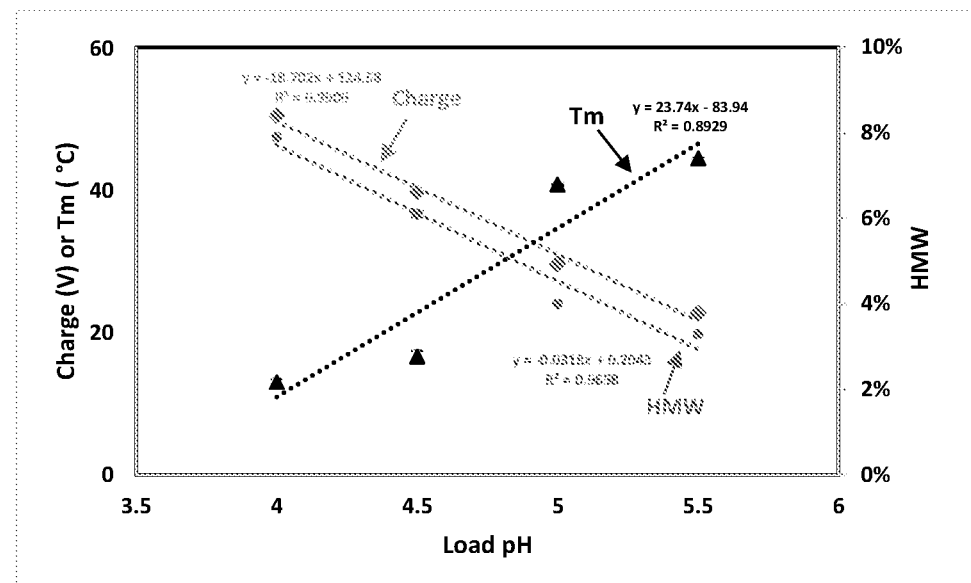
FIG. 13 shows the correlation among CEX load pH, eluate aggregate level, protein net charge, and protein melting temperature (Tm) when bound to SP SFF.

As shown in Table 2, the fitted $T_m$ value of both bound and free protein decreased with decreasing pH, suggesting that the protein became conformationally less stable at lower pH. In free solution, the $T_m$ value of the protein only showed a very minor decrease from pH 5.5 to pH 4.5, but it reduced significantly at pH 4 where the protein may have decreased structural rigidity and/or undergo major conformational changes. For bound protein, the significant decrease in $T_m$ for both resins occurred at a higher pH around pH 4.5-5.0. Results clearly indicate that, in corresponding conditions, the bound protein exposed more hydrophobic areas and became less conformationally stable than that in free solution. In addition, the $T_m$ value of the bound protein on SP SFF appeared consistently lower than that on CM SFF, suggesting lower structural stability of the protein when bound to SP SFF. This observed pattern is likely associated with overall ligand properties (e.g., type, density, linker flexibility, and etc.) as both resins have the same agarose base matrix and similar pore morphology [50]. The CEX behavior of different resins is discussed later in more detail. Combining the charge modeling with the DSF results, one can see that the increased binding strength at lower load pH caused a higher degree of protein conformational changes, more hydrophobic surface exposure and less protein structural stability, which further led to more aggregate formation in CEX. As shown in FIG. 13, the load pH is correlated reasonably well with the calculated and measured biophysical properties, as well as with the CEX eluate aggregate levels.

TABLE 2

Melting temperature ($T_m$) fitted from the DSF results with and without the presence of CEX resins in different pH conditions

| | Without resin | | With SP SFF resin [a] | | With CM SFF resin [a] | |
|---|---|---|---|---|---|---|
| $T_m$ (° C.) | Average | SD | Average | SD | Average | SD |
| pH 4 | 31.5 | 0 | 13.1 | 0.4 | 19.9 | 0.3 |
| pH 4.5 | 50.4 | 0.2 | 16.7 | 0.8 | 23.7 | 0.1 |
| pH 5 | 51.2 | 0 | 40.9 | 0.2 | 42.5 | 0.1 |
| pH 5.5 | 53.2 | 0 | 44.6 | 0 | 51.7 | 0.2 |

[a] Resin loading for both SP SFF and CM SFF are 10 g/L resin

Figure 5:
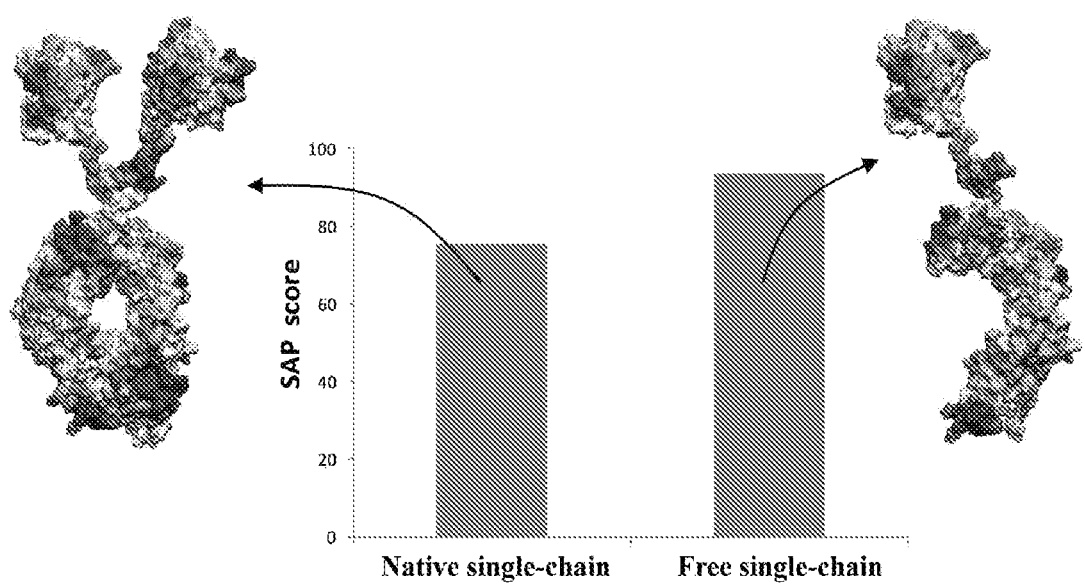
FIG. 5 shows the SAP score of the native single-chain and free single-chain. Red and blue color represents hydrophobic and hydrophilic surface areas, respectively.

For the protein studied, the conformational instability exhibited in the CEX step may be attributed to the lack of a disulfide bond between the two single chains. It has been reported that localized conformational changes can occur while the protein secondary and tertiary structure is still largely preserved on the CEX resin surface [16]. SAP modeling was employed here to explore the potential impact of small conformational changes on protein hydrophobicity. This model estimates the extent of hydrophobic regions on a solvent-exposed protein surface [37]. A simple scenario assumed was that the two single chains may separate from each other by a gap of a few angstroms (Å) upon protein adsorption onto the resin surface. When the gap allows for solvent accessibility, the hydrophobicity of the protein surface is expected to change. The surface hydrophobicity of a single chain was calculated in the native protein structure as well as in a condition without the presence of the other single chain to mimic an extreme case where the two single chains are practically separated by a gap of ≥10 Å. For both cases in SAP modeling, the secondary and tertiary structure of the single chain was kept the same. In FIG. 5, the two scenarios show appreciable differences in the distribution of the exposed hydrophobic areas. When the two single chains open up by just a small gap that allows for full solvent accessibility, the SAP score increases from 75 to 93, representing a 24% increase in protein hydrophobicity. Despite many possibilities in how the protein structure can be altered upon adsorption, the simple scenario in FIG. 5 agrees qualitatively well with the proposed hypothesis for the aggregation mechanism in CEX (FIG. 3) and with the DSF experiments where the bound protein appeared more hydrophobic than the protein in free solution. It should be noted that the SAP calculation only shows the impact of the gap between the two single chains on protein hydrophobicity, without even considering other conformational changes affecting protein secondary and tertiary structure.

3) Effect of Residence Time (RT) During Loading

The impact of the loading RT on the eluate aggregate levels was studied to explore the timescale within which conformational changes in the bound protein occurred. The total protein/resin contact time was varied by varying the loading RT (i.e., flow rate) and/or adding a static hold after the protein was loaded onto the CEX column. The elution RT was kept constant for this study. As shown in Table 3, the eluate aggregate levels increased moderately from 4.5% to 6.1% when the loading RT was changed from 2 min to 6 min, corresponding to an increase in bound protein/resin contact time from 12 min to 36 min. Longer loading RT can not only result in more protein conformational changes due to longer contact time, but also lead to higher protein concentration upon elution owing to the less significant role of intra-particle mass transfer during CEX, both of which can contribute to increased eluate aggregate levels. This phenomenon agrees well with solution studies that correlated protein-protein interactions, protein conformational stability, and aggregation rates as functions of protein concentrations [26]. Noticeably, the eluate aggregate levels increased to 17.7% with 6 min loading RT and an additional 12 h static hold, showing the significant impact of protein/resin contact time on causing severe conformational changes in the Fc-fusion protein. This observation was also reported elsewhere for IgG1 and IgG2 [12, 18]. It should be noted that the kinetics timescale of protein experiencing structural changes upon adsorption is practically relevant to normal CEX operation. Thus, the loading RT is a key factor to help control the eluate aggregate levels in CEX step, and slow loading and unnecessary hold should be avoided as much as possible for structurally unstable proteins, like the one studied in this work. It also emphasizes the importance of testing a wide range of protein/resin contact time during CEX process development to ensure robust column performance even with an unexpected on-column hold of bound product. Interestingly, no major differences in eluate aggregate levels were observed in different elution RT conditions that are of practical relevance (data not shown). This indicated that the aggregation kinetics during elution is much more rapid than the kinetics of protein experiencing conformational changes upon adsorption.

TABLE 3

Effect of residence time during loading on eluate aggregate levels in pH-step elution. The SP SFF column was loaded at 30 g/L resin at pH 4.5. SEC analysis was performed immediately upon elution.

| Loading residence time | Eluate Aggregate Level |
| --- | --- |
| 2 min | 4.5% |
| 6 min | 6.1% |
| 6 min and 12 h load hold | 17.7% |

4) Effect of CEX Resin Type

Given that protein structural changes almost always inevitably lead to changes in protein surface hydrophobicity, SP SFF, CM SFF, and Poros XS were studied in similar conditions to evaluate the impact of resin properties, particularly stationary phase hydrophobicity and ionizable ligand type. The support matrix of Poros XS and SP SFF is cross-linked poly(styrene-divinylbenzene) and cross-linked agarose, respectively. CM SFF has the same base matrix as SP SFF but the resin is functionalized with $CO_3^-$ ligand.

Figure 6A:
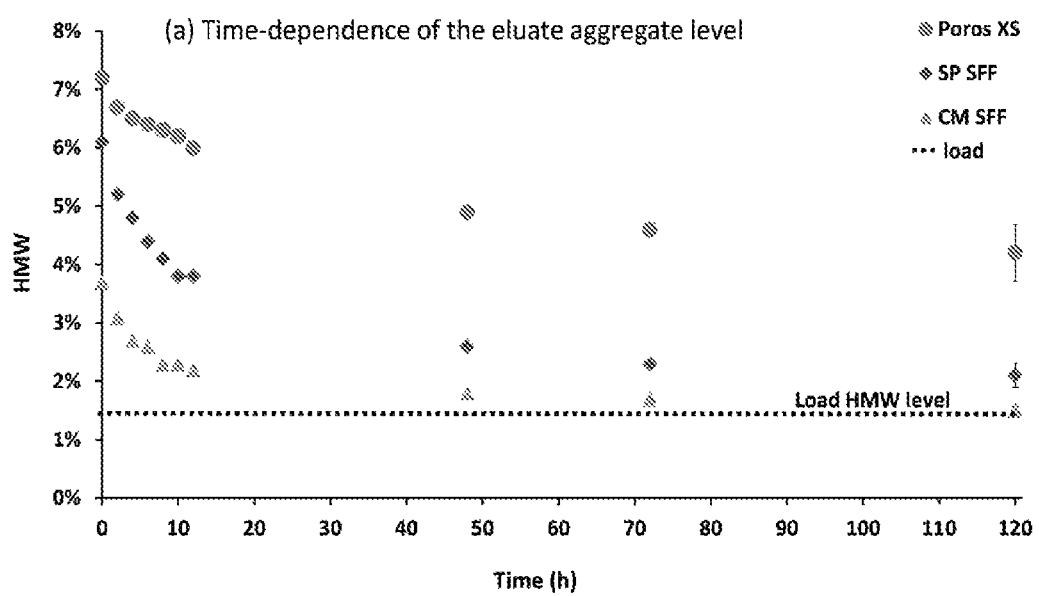
FIG. 6A shows time-dependence of the aggregate level of the pH-step eluate. All columns were loaded at 30 g/L resin at pH 4.5.
Figure 14:
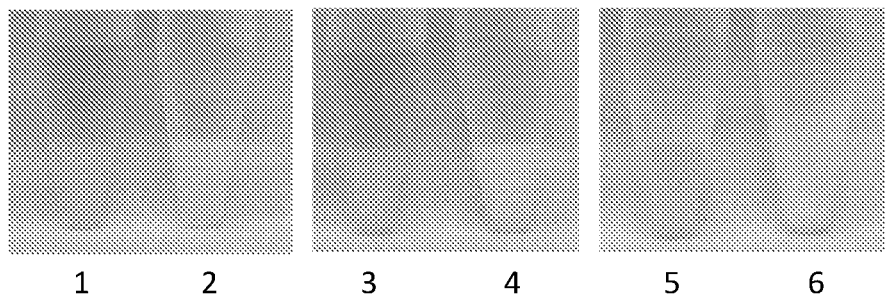
FIG. 14 shows the Sypro Orange dye experiments showing the resin hydrophobicity. Resins were incubated with Sypro Orange dye in 25 mM NaAcetate, pH 5. All the samples were inverted on a roller mixer for 5 min at 180 rpm and then gravity settled before taking pictures. Experimental conditions refer to Table 4.

As shown in FIG. 6a, the initial eluate aggregate levels varied appreciably among the three resins, with that of Poros XS (7.2%), SP SFF (6.1%) and CM SFF (3.7%) in decreasing order. It should be noted that the protein recovery from Poros XS was only 89%, much lower than SP SFF (≥98%) and CM SPP (≥98%). The remaining protein that was loaded could only be removed from the Poros XS column during a caustic cleaning step, suggesting very strong protein-resin interactions which resulted in practically irreversible binding. To better understand the differences in resin properties, Sypro Orange dye solutions were mixed with fresh resin particles in the conditions listed in Table 4. As shown in FIG. 14, CM SFF and SP SFF showed very minor dye binding based on the light color change in the resin phase before and after adding the dye, probably due mainly to the known hydrophilic nature of the agarose base matrix. On the contrary, Poros XS showed significant dye binding, as suggested by the change in resin color. This clearly indicates that, despite its hydrophilic coating, Poros XS is still sufficiently hydrophobic to bind the hydrophobic dye. Compared to CM SPP and SP SFF, Poros XS can interact more strongly with the bound protein via the secondary hydrophobic interactions between protein and resin, which also explains the higher percentage of irreversible binding and aggregate formation in Poros XS eluate. However, it should be noted that it is difficult to attribute the observed trend to specific factor(s) because the impacts of different ligand densities, linker properties, pore structures and hydrophobicity of base matrix are confounding variables for different resins.

TABLE 4

Labeling conditions of the Sypro Orange dye experiments

| Sample # | Resin | Sypro Orange Dye Concentration |
| --- | --- | --- |
| 1 | CM SFF | 15× |
| 2 | CM SFF | 0× |
| 3 | SP SFF | 15× |
| 4 | SP SFF | 0× |
| 5 | Poros XS | 15× |
| 6 | Poros XS | 0× |

Figure 6B:
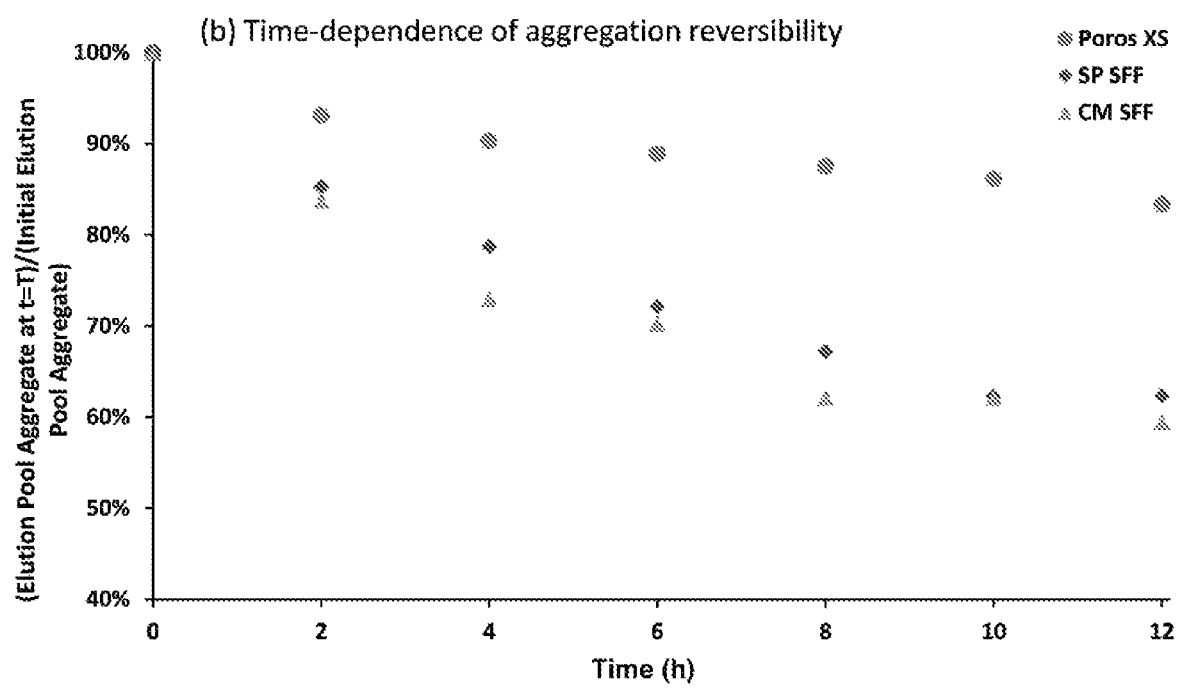
FIG. 6B shows time-dependence of aggregation reversibility for different resins. All columns were loaded at 30 g/L resin at pH 4.5.

Another observation in FIG. 6 is the comparison of the aggregation reversibility for the three resins studied. As shown in FIG. 6a, the eluate aggregate levels for CM SFF and SP SFF decreased to less than 2%, while that for Poros XS was still around 4% even after 120 h. Furthermore, the aggregates formed during the Poros XS elution reverted to monomer to a significantly lesser extent (thermodynamic aspect) and at a much slower rate (kinetic aspect) as shown in FIG. 6b. The aggregates in the CM SFF and SP SFF eluate showed a similar degree of reversibility, suggesting perhaps similar biophysical properties. The obvious difference in the aggregation reversibility between Poros XS and the other two resins reflected the much stronger overall protein-resin interactions (including protein/ligand and protein/resin surface) on Poros XS, leading to different molecular properties of the formed aggregate species.

4. Experimental Verification of the Proposed Mechanism

Various strategies have been tested to reduce or prevent aggregate formation in the CEX step. The use of macroporous resins with no grafted polymer, such as UNOsphere Rapid, was found to be effective in reducing CEX-induced product unfolding and aggregation for mAbs [17]. However, this resin was not able to mitigate the aggregate formation under the conditions evaluated in this work (data not shown). Adding excipients (e.g., arginine, glycine and sucrose) to the load/wash/elution solutions was also proved ineffective. These results imply a different aggregation mechanism from the other earlier studies. According to the proposed hypothesis, the aggregate formation is the result of the severity of the conformational changes in the bound protein and the concentration of the aggregation-prone protein upon elution. Thus, measures such as high load pH, short protein/resin contact time, hydrophilic resin surface, and weak ionizable ligands can help reduce the aggregate formation. Nevertheless, none of these efforts was able to completely prevent aggregate formation in this study.

Figure 7:
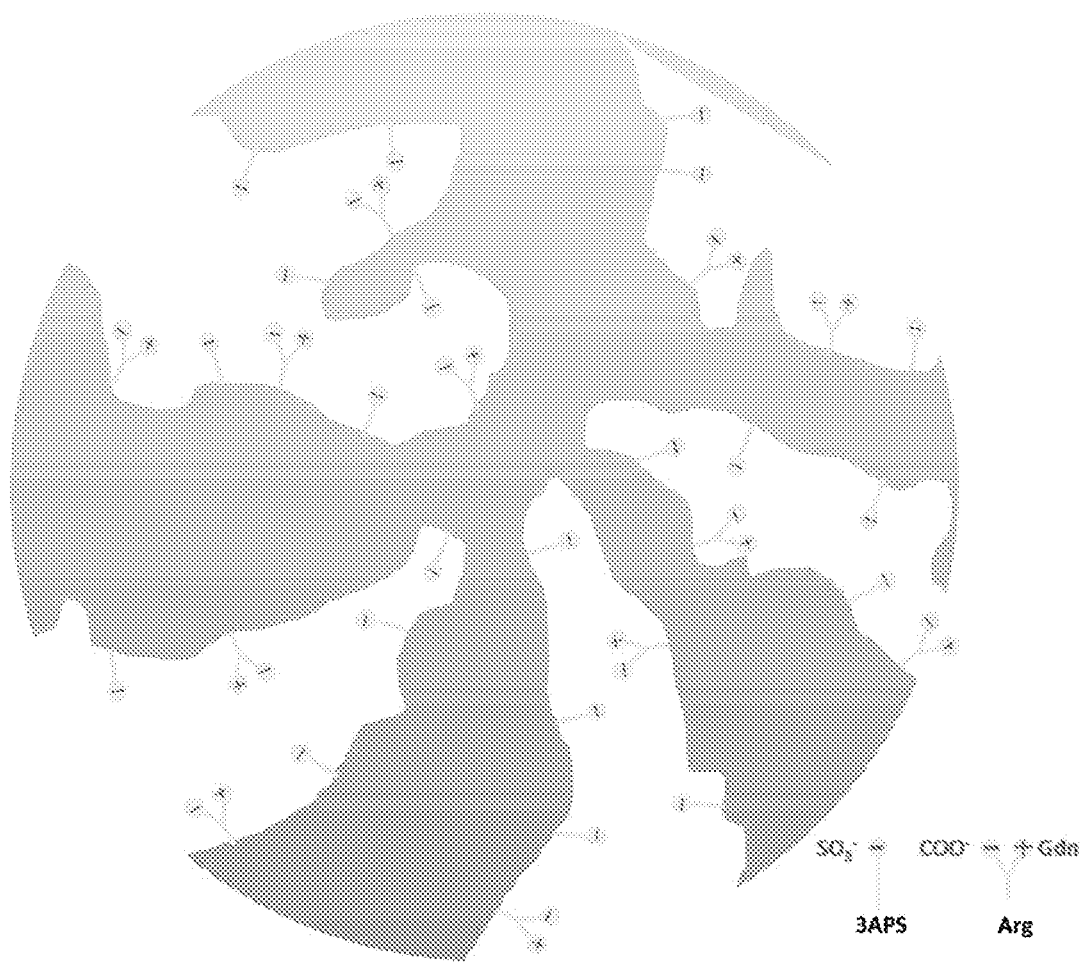
FIG. 7 shows the schematic drawings of the Arg-SP mixed mode agarose bead.

In addition to the readily applicable measures evaluated above, resin modifications were carried out to examine the proposed aggregation hypothesis and to gain mechanistic understanding of the aggregation phenomenon at a molecular level. Custom-made resins (functionalized with SP and Arg-SP ligands) were prepared in-house at relatively low SP ligand density, with and without additionally immobilizing arginine to the resin surface to create secondary protein-arginine interactions in close proximity to the resin surface. The dynamic binding capacity for fully functionalized SP agarose resin is 30 g/L resin, lower than that for SP SFF (≥50 g/L resin) when measured in the same condition. The dynamic binding capacity for the prepared Arg-SP agarose resin is 20 g/L resin due to the weakening effect of immobilized arginine. Despite its wide use as a protein stabilizer in solutions, arginine has not been immobilized onto a resin surface to modulate the primary protein-resin attractions with permanent secondary protein-arginine interactions. FIG. 7 shows the schematic drawing of the Arg-SP modified mixed-mode agarose bead.

Figure 8:
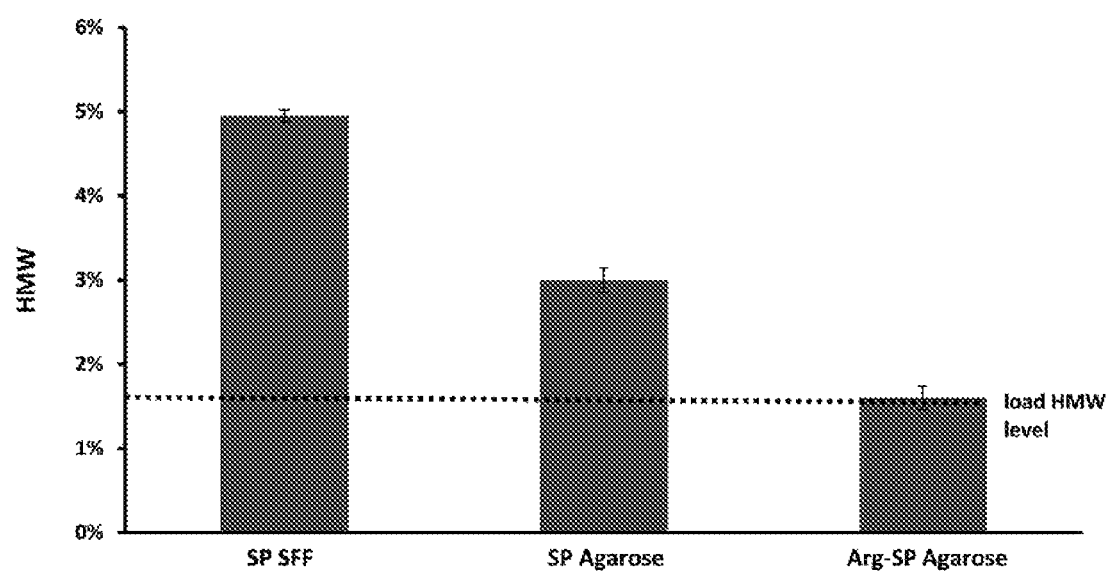
FIG. 8 shows the aggregate level of the pH-step eluate with different resins. The CEX column was loaded at 10 g/L resin at pH 4.5, and eluted with 50 mM NaAcetate, pH 8.3 buffer.

Comparison of several different resins including the two custom-made ones is shown in FIG. 8. It can be seen that aggregate formation from the SP agarose resin was lower compared to SP SFF. This was believed to be mainly due to the relatively lower ligand density in the custom-made SP agarose resin, as suggested by a recent molecular-scale investigation where stochastic ligand distribution in various clustering conditions led to different protein adsorption properties even for chemically identical ligands [51]. Lower ligand density resulted in a smaller number of interacting ligands per bound protein and helped reduce the aggregate formation to a certain extent. For the Arg-SP agarose resin, no appreciable aggregate increase was observed in the eluate. This may be due to the weakening effect of the immobilized arginine on protein-resin interactions. The immobilized arginine may practically serve as a mixed-charge ligand (i.e., negatively charged carboxylic group and positive charged guanidine group), which can hinder undesirable interactions between bound protein and resin surface. The positively charged guanidine group in the immobilized arginine can contribute to weaker binding strength and less protein conformational changes. It is noted that the weakening effect of arginine on protein-resin interactions appeared effective only when arginine was immobilized onto the resin surface where it functioned as a mixed-mode ligand instead of a free solute. The difference in the impact of arginine may suggest the unique advantage of using arginine as a mixed-mode ligand to mitigate the aggregation issue for structurally unstable proteins in CEX. It is unclear if the guanidine group on the immobilized arginine has an additional protein stabilizing effect similar to that observed when adding arginine to protein solutions [52]. The answer to this question is outside the scope of this work, and would require additional studies involving the immobilization of different molecules with appropriately selected functional groups. While the immobilization procedure is being further optimized (a separate effort) to improve the binding capacity and retain the HMW mitigation ability, the results obtained here provide supportive evidence for the proposed hypothesis.

CONCLUSION

This work investigated the aggregation behavior of a structurally unstable Fc-fusion in the CEX step. The multi-peak elution profile using a salt-step elution was found to be associated with aggregate formation caused by protein stability properties during intra-column buffer transition. Single-peak elution was achieved by using a pH-step elution, whereas aggregation occurred via a different mechanism originating from the conformational changes of bound protein. The pH-step elution data explicitly shows the impact of CEX bind/elute process on protein conformational stability and aggregation propensity in solution conditions where the molecule would be stable. The aggregates formed can be thermodynamically unfavorable and partially reverted to native conformation within several days in the conditions studied. The relatively slow aggregate dissociation kinetics emphasizes the importance of proper and consistent practice of sampling, sample storage, and analytical testing to ensure representative and reproducible analytical results. Aggregate formation was found to be sensitive to CEX column loading which affected the severity of the conformational changes for bound protein and the concentration of the aggregation-prone proteins upon elution. These two factors together contributed to the nonlinear pattern of the eluate aggregate levels as a function of column loading.

Aggregate formation and stability in CEX eluate can also be affected by other operating conditions (e.g., pH, flow rate, etc.) as well as resin properties. In general, those practical measures to reduce protein binding strength and protein-resin contact time can lead to lower aggregate levels due to less conformational changes in bound protein, as confirmed by the DSF results. Preferred resin properties include weak ionizable ligand (e.g., CM functionality), hydrophilic resin surface, and lower ligand density. The study using the Arg-SP agarose resin prepared in-house provides an experimental verification of the proposed hypothesis for the aggregation behavior seen in the CEX step. Immobilizing arginine onto the resin surface effectively minimized the undesirable interactions between protein and resin even at low pH conditions where the protein exhibited structural instability and high eluate aggregate levels using all the other CEX resins evaluated. This work not only sheds light on enhancing the mechanistic understanding of the aggregate formation for structurally unstable Fc-fusion proteins in the CEX step, but also provides some interesting directions in new resin design for special applications, such as the one studied here. Finally, the inconsistency between the protein stability property observed in solutions and its aggregation propensity in chromatography process emphasizes the importance of acquiring molecules' downstream processibility information (i.e., this study) in designing manufacturing-friendly biologic molecules and in developing robust CEX polishing processes.

REFERENCES

[1] J. M. Reichert, Monoclonal antibodies as innovative therapeutics, Curr. Pharm. Biotechnol. 9 (2008) 423-430.

[2] D. M. Ecker, S. D. Jones, H. L. Levine, The therapeutic monoclonal antibody market, mAbs 7 (2015) 9-14.

[3] Z. Chen, T. Chen, X. Sun, B. J. Hinds, Dynamic Electrochemical Membranes for Continuous Affinity Protein Separation, Adv. Funct. Mater. 24 (2014) 4317-4323.

[4] A. A. Shukla, B. Hubbard, T. Tressel, S. Guhan, D. Low, Downstream processing of monoclonal antibodies—application of platform approaches, J. Chromatogr. B 848 (2007) 28-39.

[5] A. Staby, M. B. Sand, R. G. Hansen, J. H. Jacobsen, L. A. Andersen, M. Gerstenberg, U. K. Bruus, I. H. Jensen, Comparison of chromatographic ion-exchange resins IV. Strong and weak cation-exchange resins and heparin resins, J. Chromatogr. A 1069 (2005) 65-77.

[6] L. Yu, L. Zhang, Y. Sun, Protein behavior at surfaces: orientation, conformational transitions and transport, J. Chromatogr. A 1382 (2015) 118-134.

[7] A. Jungbauer, C. Machold, R. Hahn, Hydrophobic interaction chromatography of proteins. III. Unfolding of proteins upon adsorption, J. Chromatogr. A 1079 (2005) 221-228.

[8] Y. Xiao, A. Rathore, J. P. O'Connell, E. J. Fernandez, Generalizing a two-conformation model for describing salt and temperature effects on protein retention and stability in hydrophobic interaction chromatography, J. Chromatogr. A 1157 (2007) 197-206.

[9] L. Zhang, G. Zhao, Y. Sun, Molecular insight into protein conformational transition in hydrophobic charge induction chromatography: a molecular dynamics simulation, J. Phys. Chem. B 113 (2009) 6873-6880.

[10] A. Voitl, A. Butte, M. Morbidelli, Behavior of human serum albumin on strong cation exchange resins: II. model analysis, J. Chromatogr. A 1217 (2010) 5492-5500.

[11] A. Voitl, A. Butte, M. Morbidelli, Behavior of human serum albumin on strong cation exchange resins: I. experimental analysis, J. Chromatogr. A 1217 (2010) 5484-5491.

[12] R. Gillespie, T. Nguyen, S. Macneil, L. Jones, S. Crampton, S. Vunnum, Cation exchange surface-mediated denaturation of an aglycosylated immunoglobulin (IgG1), J. Chromatogr. A 1251 (2012) 101-110.

[13] T. Arakawa, D. Ejima, K. Tsumoto, N. Obeyama, Y. Tanaka, Y. Kita, S. N. Timasheff, Suppression of protein interactions by arginine: a proposed mechanism of the arginine effects, Biophys. Chem. 127 (2007) 1-8.

[14] U. Das, G. Hariprasad, A. S. Ethayathulla, P. Manral, T. K. Das, S. Pasha, A. Mann, M. Ganguli, A. K. Verma, R. Bhat, S. K. Chandrayan, S. Ahmed, S. Sharma, P. Kaur, T. P. Singh, A. Srinivasan, Inhibition of protein aggregation: supramolecular assemblies of arginine hold the key, PloS one, 2 (2007) e1176.

[15] M. T. Gao, X. Y. Dong, Y. Sun, Interactions between L-arginine/L-arginine derivatives and lysozyme and implications to their inhibition effects on protein aggregation, Biotechnol. Prog. 29 (2013) 1316-1324.

[16] J. Guo, G. Carta, Unfolding and aggregation of a glycosylated monoclonal antibody on a cation exchange column. Part II. Protein structure effects by hydrogen deuterium exchange mass spectrometry, J. Chromatogr. A 1356 (2014) 129-137.

[17] J. Guo, G. Carta, Unfolding and aggregation of monoclonal antibodies on cation exchange columns: effects of resin type, load buffer, and protein stability, J. Chromatogr. A 1388 (2015) 184-194.

[18] J. Guo, S. Zhang, G. Carta, Unfolding and aggregation of a glycosylated monoclonal antibody on a cation exchange column. Part I. Chromatographic elution and batch adsorption behavior, J. Chromatogr. A 1356 (2014) 117-128.

[19] H. Luo, N. Macapagal, K. Newell, A. Man, A. Parupudi, Y. Li, Y. Li, Effects of salt-induced reversible self-association on the elution behavior of a monoclonal antibody in cation exchange chromatography, J. Chromatogr. A 1362 (2014) 186-193.

[20] H. Luo, M. Cao, K. Newell, C. Afdahl, J. Wang, W. K. Wang, Y. Li, Double-peak elution profile of a monoclonal antibody in cation exchange chromatography is caused by histidine-protonation-based charge variants, J. Chromatogr. A 1424 (2015) 92-101.

[21] W. Wang, S. Singh, D. L. Zeng, K. King, S. Nema, Antibody structure, instability, and formulation, J. Pharm. Sci. 96 (2007) 1-26.

[22] A. L. Fink, L. J. Calciano, Y. Goto, T. Kurotsu, D. R. Palleros, Classification of acid denaturation of proteins: intermediates and unfolded states, Biochemistry, 33 (1994) 12504-12511.

[23] J. Buchner, M. Renner, H. Lilie, H. J. Hinz, R. Jaenicke, T. Kiefhabel, R. Rudolph, Alternatively folded states of an immunoglobulin, Biochemistry, 30 (1991) 6922-6929.

[24] S. B. Hari, H. Lau, V. I. Razinkov, S. Chen, R. F. Latypov, Acid-induced aggregation of human monoclonal IgG1 and IgG2: molecular mechanism and the effect of solution composition, Biochemistry, 49 (2010) 9328-9338.

[25] R. F. Latypov, S. Hogan, H. Lau, H. Gadgil, D. Liu, Elucidation of acid-induced unfolding and aggregation of human immunoglobulin IgG1 and IgG2 Fc, J. Biol. Chem. 287 (2012) 1381-1396.

[26] R. Ghosh, C. Calero-Rubio, A. Saluja, C. J. Roberts, Relating Protein-Protein Interactions and Aggregation Rates From Low to High Concentrations, J. Pharm. Sci. 105 (2016) 1086-1096.

[27] C. J. Roberts, Non-native protein aggregation kinetics, Biotechnol. Bioeng. 98 (2007) 927-938.

[28] E. J. Yearley, P. D. Godfrin, T. Perevozchikova, H. Zhang, P. Falus, L. Porcar, M. Nagao, J. E. Curtis, P. Gawande, R. Taing, I. E. Zarraga, N. J. Wagner, Y. Liu, Observation of small cluster formation in concentrated monoclonal antibody solutions and its implications to solution viscosity, Biophys. J. 106 (2014) 1763-1770.

[29] S. Yadav, T. M. Laue, D. S. Kalonia, S. N. Singh, S. J. Shire, The influence of charge distribution on self-association and viscosity behavior of monoclonal antibody solutions, Mol. Pharm. 9 (2012) 791-802.

[30] A. Chaudhri, I. E. Zarraga, T. J. Kamerzell, J. P. Brandt, T. W. Patapoff, S. J. Shire, G. A. Voth, Coarse-grained modeling of the self-association of therapeutic monoclonal antibodies, J. Phys. Chem. B 116 (2012) 8045-8057.

[31] J. L. Fast, A. A. Cordes, J. F. Carpenter, T. W. Randolph, Physical instability of a therapeutic Fc fusion protein: domain contributions to conformational and colloidal stability, Biochemistry, 48 (2009) 11724-11736.

[32] S. Ghose, T. M. McNerney, B. Hubbard, pH Transitions in ion-exchange systems: role in the development of a cation-exchange process for a recombinant protein, Biotechnol. Prog. 18 (2002) 530-537.

[33] T. M. Pabst, G. Carta, pH transitions in cation exchange chromatographic columns containing weak acid groups, J. Chromatogr. A 1142 (2007) 19-31.

[34] J. S. Perez, D. D. Frey, Behavior of the inadvertent pH transient formed by a salt gradient in the ion-exchange chromatography of proteins, Biotechnol. Prog. 21 (2005) 902-910.

[35] F. Wang, S. Sen, Y. Zhang, I. Ahmad, X. Zhu, I. A. Wilson, V. V. Smider, T. J. Magliery, P. G. Schultz, Somatic hypermutation maintains antibody thermodynamic stability during affinity maturation, Proc. Natl. Acad. Sci. USA 110 (2013) 4261-4266.

[36] BIOVIA Software Inc., Discovery Studio Modeling Environment, Release 4.1, San Diego: BIOVIA Software Inc., 2014.

[37] N. Chennamsetty, V. Voynov, V. Kayser, B. Helk, B. L. Trout, Design of therapeutic proteins with enhanced stability, Proc. Natl. Acad. Sci. USA 106 (2009) 11937-11942.

[38] S. D. Black, D. R. Mould, Development of hydrophobicity parameters to analyze proteins which bear post- or cotranslational modifications, Anal. Biochem. 193 (1991) 72-82.

[39] A. D. MacKerell, D. Bashford, M. Bellott, R. L. Dunbrack, J. D. Evanseck, M. J. Field, S. Fischer, J. Gao, H. Guo, S. Ha, D. Joseph-McCarthy, L. Kuchnir, K. Kuczera, F. T. Lau, C. Mattos, S. Michnick, T. Ngo, D. T. Nguyen, B. Prodhom, W. E. Reiher, B. Roux, M. Schlenkrich, J. C. Smith, R. Stote, J. Straub, M. Watanabe, J. Wiorkiewicz-Kuczera, D. Yin, M. Karplus, All-atom empirical potential for molecular modeling and dynamics studies of proteins, J. Phys. Chem. B 102 (1998) 3586-3616.

[40] D. S. Tomar, S. Kumar, S. K. Singh, S. Goswami, L. Li, Molecular basis of high viscosity in concentrated antibody solutions: Strategies for high concentration drug product development, mAbs, 8 (2016) 216-228.

[41] R. Chaudhuri, Y. Cheng, C. R. Middaugh, D. B. Volkin, High-throughput biophysical analysis of protein therapeutics to examine interrelationships between aggregate formation and conformational stability, AAPS J. 16 (2014) 48-64.

[42] E. Y. Chi, S. Krishnan, T. W. Randolph, J. F. Carpenter, Physical stability of proteins in aqueous solution: mechanism and driving forces in nonnative protein aggregation, Pharm. Res. 20 (2003) 1325-1336.

[43] C. Chang, A. M. Lenhoff, Comparison of protein adsorption isotherms and uptake rates in preparative cation-exchange materials, J. Chromatogr. A 827 (1998) 281-293.

[44] A. Chaudhri, I. E. Zarraga, S. Yadav, T. W. Patapoff, S. J. Shire, G. A. Voth, The Role of Amino Acid Sequence in the Self-Association of Therapeutic Monoclonal Antibodies: Insights from Coarse-Grained Modeling, J. Phys. Chem. B 117 (2013) 1269-1279.

[45] J. M. Perchiacca, C. C. Lee, P. M. Tessier, Optimal charged mutations in the complementarity-determining regions that prevent domain antibody aggregation are dependent on the antibody scaffold, Protein Eng. Des. Sel. 27 (2014) 29-39.

[46] S. J. Shire, Formulation and manufacturability of biologics, Curr. Opin. Biotechnol. 20 (2009) 708-714.

[47] F. H. Niesen, H. Berglund, M. Vedadi, The use of differential scanning fluorimetry to detect ligand interactions that promote protein stability, Nat. Protoc. 2 (2007) 2212-2221.

[48] C. R. C. Reichardt, Solvents and solvent effects in organic chemistry, VCH, Weinheim, 1988.

[49] F. Vollrath, N. Hawkins, D. Porter, C. Holland, M. Boulet-Audet, Differential Scanning Fluorimetry provides high throughput data on silk protein transitions, Sci. Rep. 4 (2014) 5625.

[50] P. DePhillips, A. M. Lenhoff, Pore size distributions of cation-exchange adsorbents determined by inverse size-exclusion chromatography, J. Chromatogr. A 883 (2000) 39-54.

[51] L. Kisley, J. Chen, A. P. Mansur, B. Shuang, K. Kourentzi, M.-V. Poongavanam, W.-H. Chen, S. Dhamane, R. C. Willson, C. F. Landes, Unified superresolution experiments and stochastic theory provide mechanistic insight into protein ion-exchange adsorptive separations, Proc. Natl. Acad. Sci. USA 111 (2014) 2075-2080.

[52] B. M. Baynes, D. I. Wang, B. L. Trout, Role of arginine in the stabilization of proteins against aggregation, Biochemistry, 44 (2005) 4919-4925.

We claim:

1. A cation exchange (CEX) resin chemically coupled with arginine for use in chromatography.

2. The CEX resin of claim 1, wherein the CEX resin is selected from agarose, cellulose, dextran, chitosan, poly (methacrylate), acrylic polymers, and poly(styrene-divinylbenzene).

3. The CEX resin of claim 1, wherein the CEX resin is prepared using a cation exchange ligand selected from sulfonate, carboxylic, carboxymethyl sulfonic acid, sulfoisobutyl, sulfoethyl, carboxyl, sulphopropyl, sulphonyl, sulphoxyethyl and orthophosphate.

4. The CEX resin of claim 1, wherein the CEX resin coupled with arginine is an arginine-sulphopropyl (Arg-SP) functionalized resin.

* * * * *